(12) United States Patent
Ebi

(10) Patent No.: US 9,546,934 B2
(45) Date of Patent: Jan. 17, 2017

(54) FILTER MEMBER AND A METHOD OF OBTAINING CELLS USING THE SAME

(71) Applicant: SYSMEX CORPORATION, Kobe-shi, Hyogo (JP)

(72) Inventor: Ryuichiro Ebi, Osaka (JP)

(73) Assignee: SYSMEX CORPORATION, Kobe-shi (JP)

( * ) Notice: Subject to any disclaimer, the term of this patent is extended or adjusted under 35 U.S.C. 154(b) by 9 days.

(21) Appl. No.: 14/489,060

(22) Filed: Sep. 17, 2014

(65) Prior Publication Data

US 2015/0087010 A1 Mar. 26, 2015

(30) Foreign Application Priority Data

Sep. 26, 2013 (JP) ................................. 2013-199719

(51) Int. Cl.
  *B01D 35/00* (2006.01)
  *G01N 1/31* (2006.01)
  (Continued)

(52) U.S. Cl.
  CPC ............... *G01N 1/31* (2013.01); *B01D 29/055* (2013.01); *B01D 39/10* (2013.01); *B01L 3/502* (2013.01); *G01N 15/1459* (2013.01); *G01N 35/1095* (2013.01); *B01L 2200/0689* (2013.01); *B01L 2300/0618* (2013.01); *B01L 2300/0681* (2013.01); *B01L 2400/0487* (2013.01); *G01N 2015/1006* (2013.01);
  (Continued)

(58) Field of Classification Search
  USPC ........................................................ 422/534
  See application file for complete search history.

(56) References Cited

U.S. PATENT DOCUMENTS 3,985,032 A * 10/1976 Avakian ................ B01L 3/0275
  422/513
6,051,393 A *  4/2000 Jones ............... G01N 33/57411
  424/9.1

(Continued)

FOREIGN PATENT DOCUMENTS

EP      0 806 475 A3   1/2001
EP      2 306 171 A2   4/2011
WO    2008/107652 A1   9/2008

*Primary Examiner* — Jill Warden
*Assistant Examiner* — Brittany Fisher
(74) *Attorney, Agent, or Firm* — Mots Law, PLLC

(57) ABSTRACT

The present invention provides a filter member. The filter member comprises: a filter for discriminating cells to be analyzed in a sample from other components; a first filter holding member which comprises a first through hole and has a plate-like shape; and a second filter holding member which comprises a second through hole and is fitted into the first filter holding member. When the first and second filter holding members are integrated by fitting the second filter holding member into the first filter holding member, the filter is sandwiched between the first filter holding member and the second filter holding member, and the first through hole is opposed to the second through hole through the filter. A first elastic body is formed on a surface of the first filter holding member, the surface being in contact with the filter. A second elastic body is formed on a surface of the second filter holding member, the surface being in contact with the filter.

19 Claims, 19 Drawing Sheets

(51) Int. Cl.
   B01D 39/10 (2006.01)
   B01D 29/05 (2006.01)
   G01N 35/10 (2006.01)
   B01L 3/00 (2006.01)
   G01N 15/10 (2006.01)
   G01N 15/14 (2006.01)
   G01N 35/00 (2006.01)
   G01N 35/04 (2006.01)

(52) U.S. Cl.
   CPC ............... *G01N 2015/1486* (2013.01); *G01N 2035/00346* (2013.01); *G01N 2035/0412* (2013.01); *G01N 2035/0439* (2013.01); *G01N 2035/0444* (2013.01)

(56) References Cited

U.S. PATENT DOCUMENTS

| | | | | |
|---|---|---|---|---|
| 6,139,757 A | * | 10/2000 | Ohmura | B01D 61/18 210/351 |
| 6,296,764 B1 | * | 10/2001 | Guirguis | G01N 1/2813 210/319 |
| 6,884,341 B2 | * | 4/2005 | Ferguson | G01N 1/2813 137/550 |
| 2004/0014023 A1 | * | 1/2004 | Meserol | C12Q 1/001 435/2 |
| 2008/0108103 A1 | | 5/2008 | Ishisaka et al. | |
| 2010/0089815 A1 | * | 4/2010 | Zhang | B01L 3/502753 210/335 |
| 2011/0076755 A1 | | 3/2011 | Ebi et al. | |
| 2013/0242012 A1 | * | 9/2013 | Hayashi | B41J 2/17563 347/93 |
| 2015/0087010 A1 | * | 3/2015 | Ebi | B01D 29/055 435/30 |

* cited by examiner

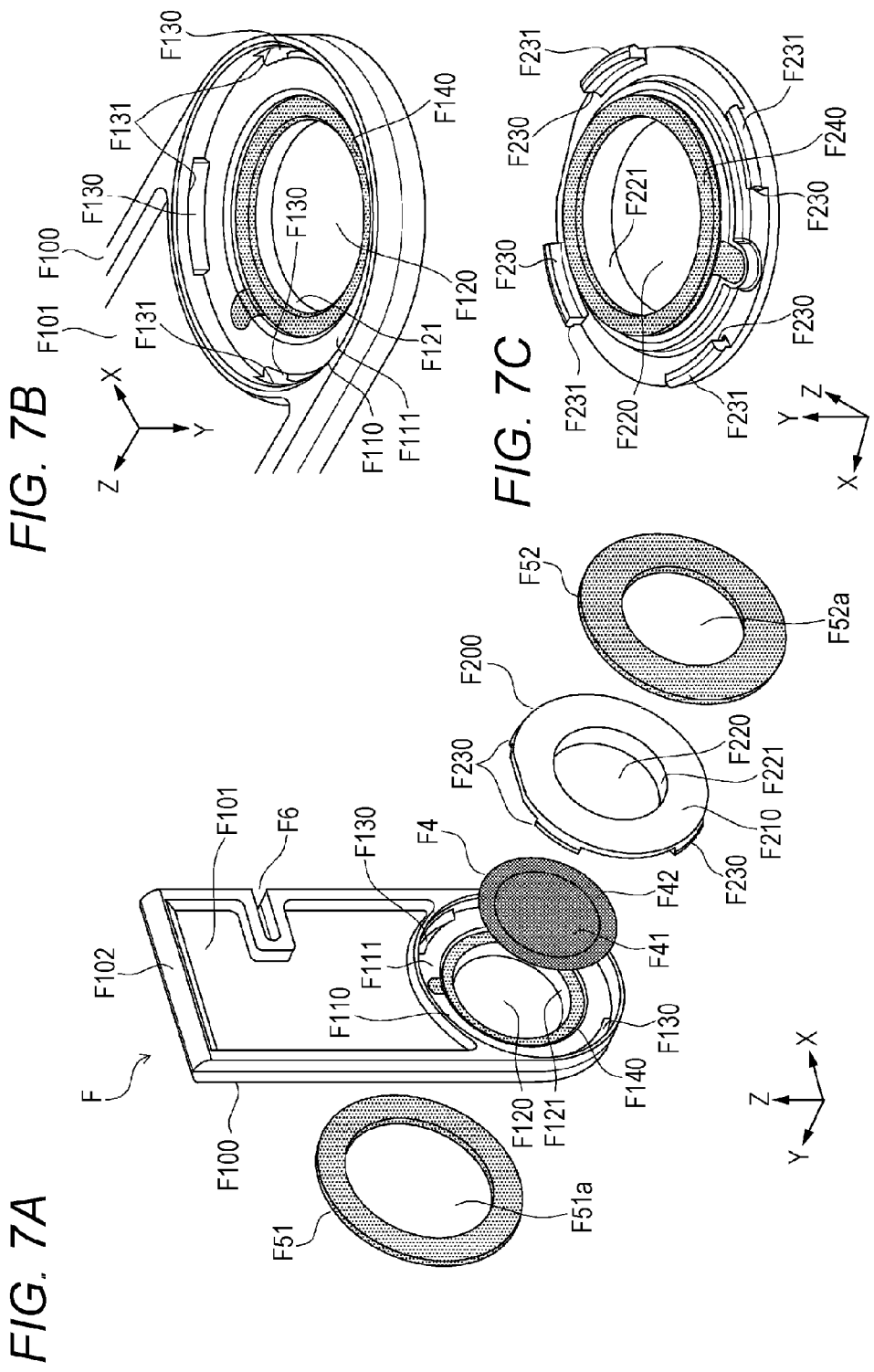

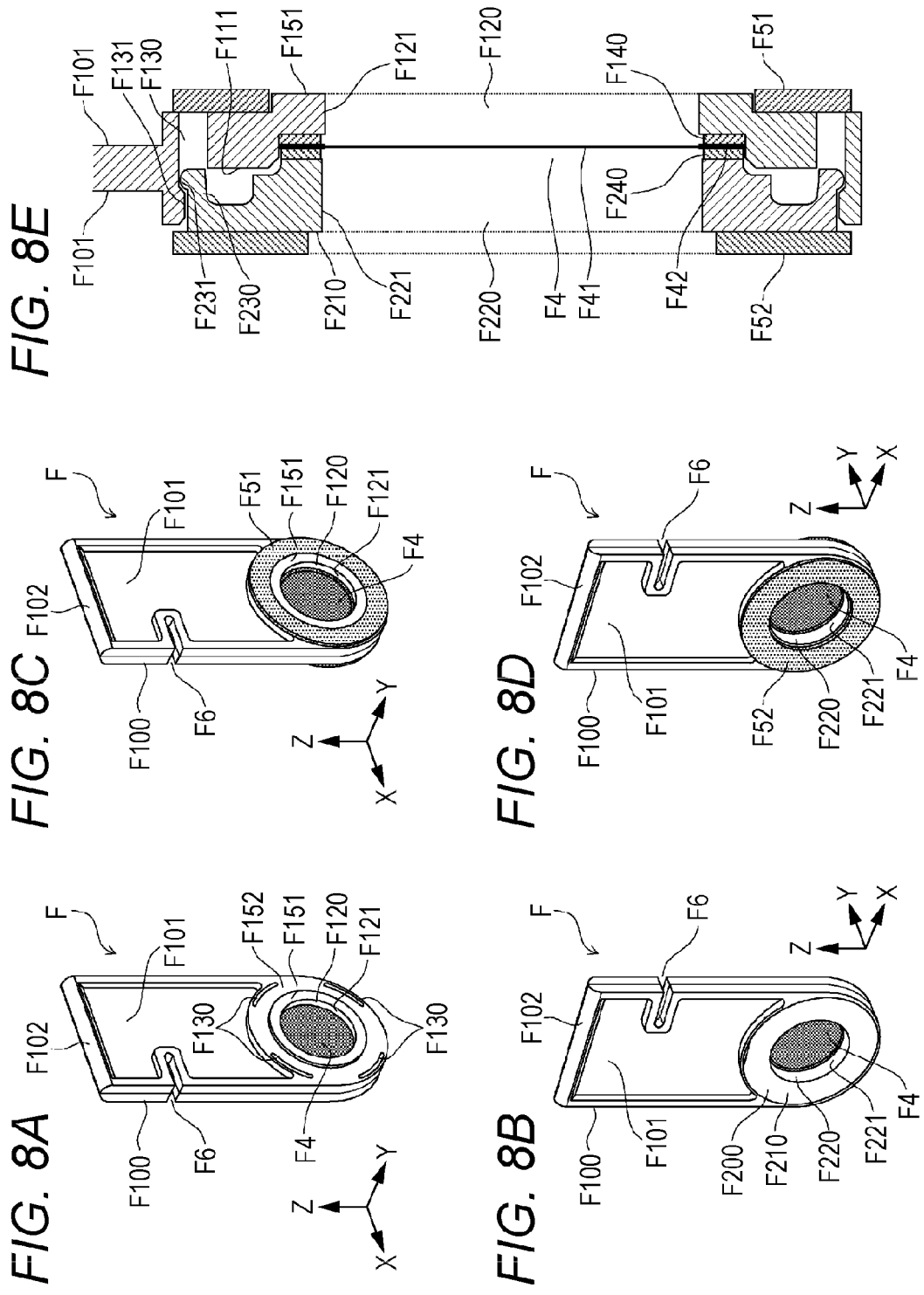

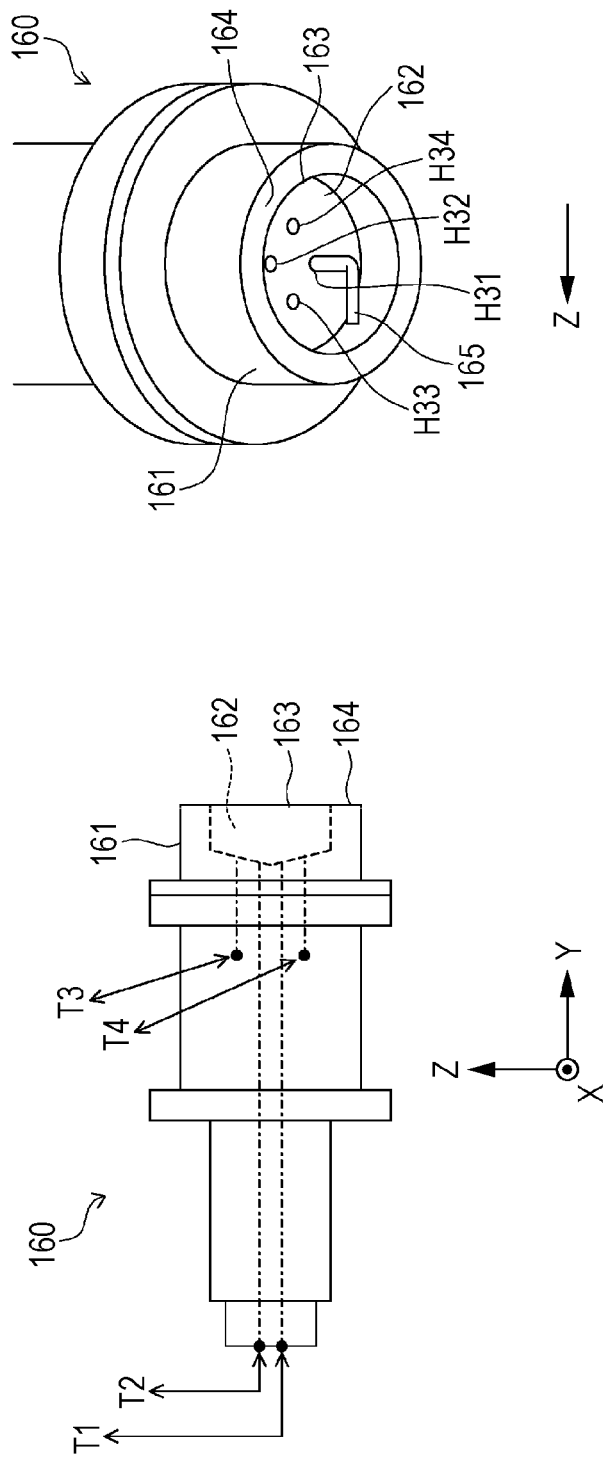

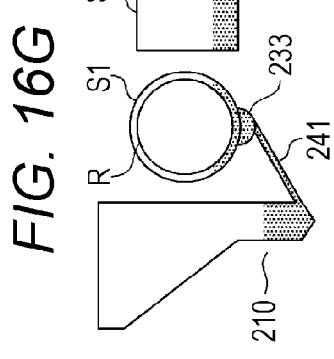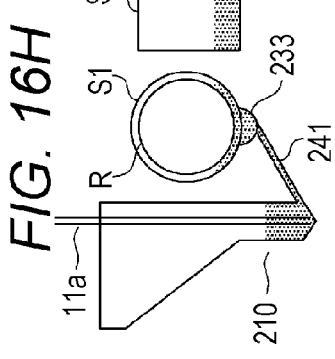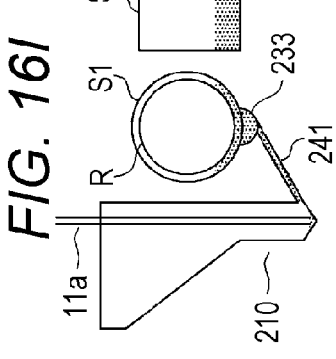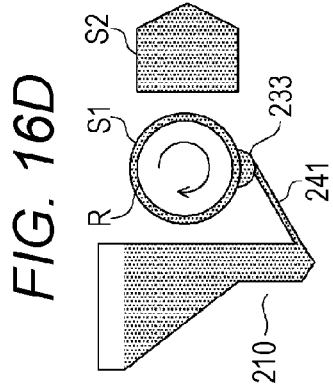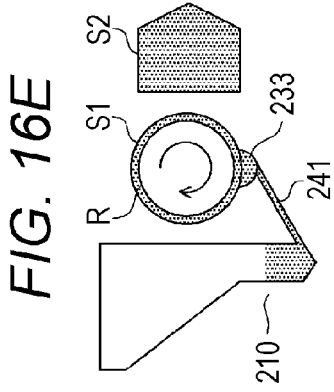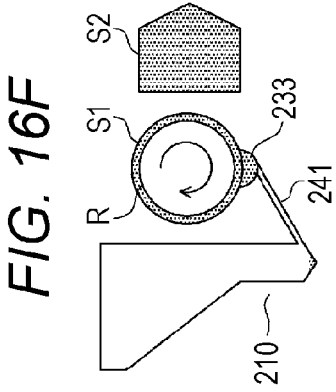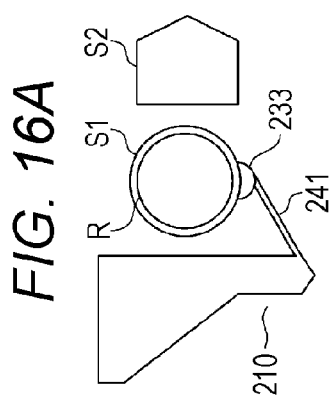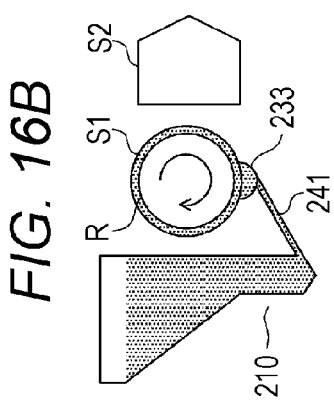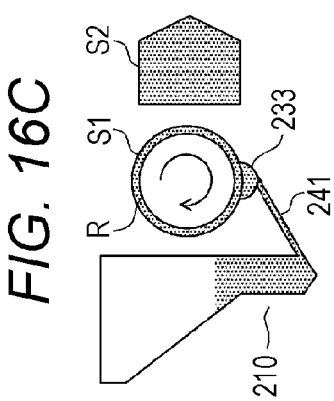

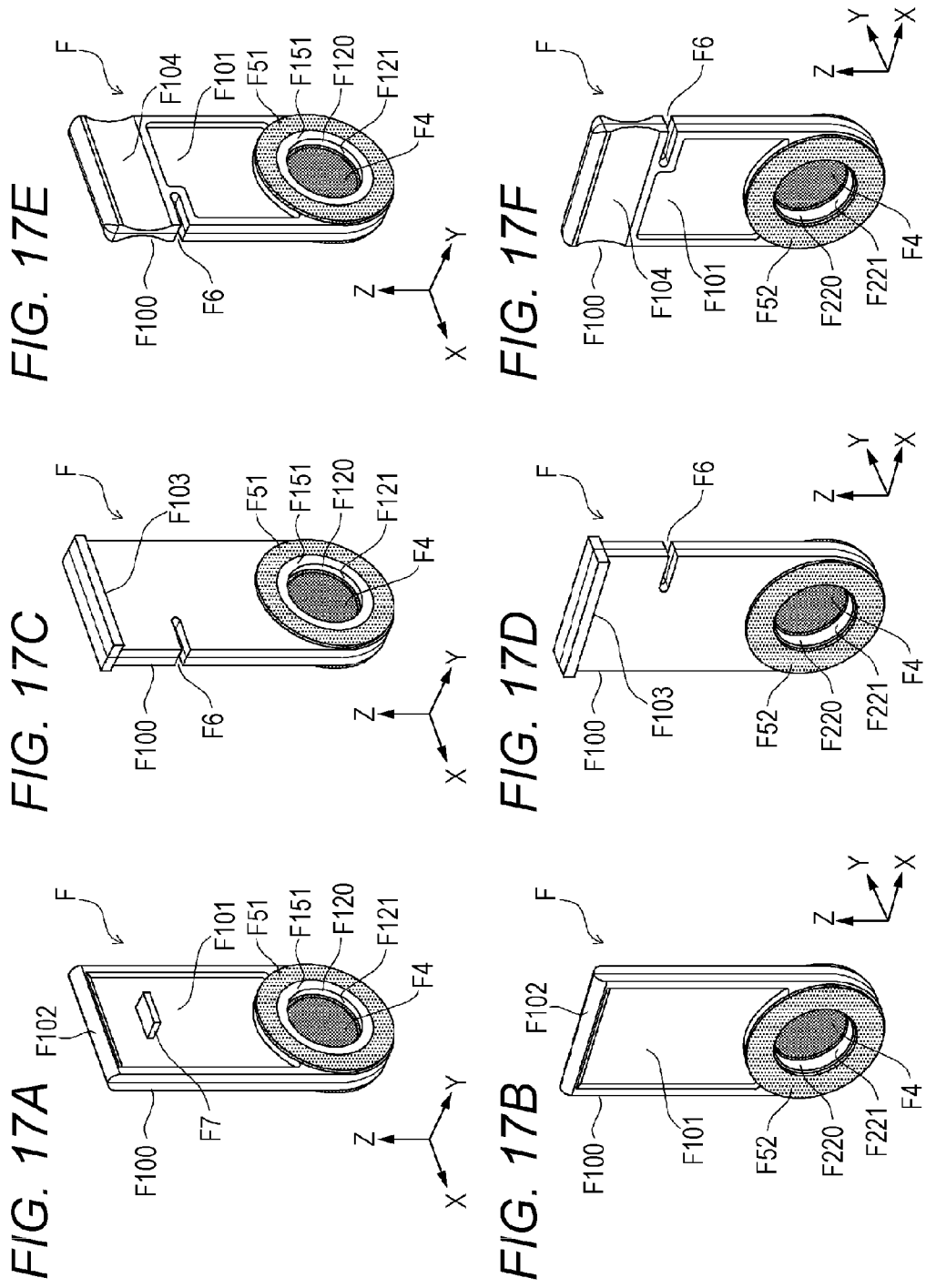

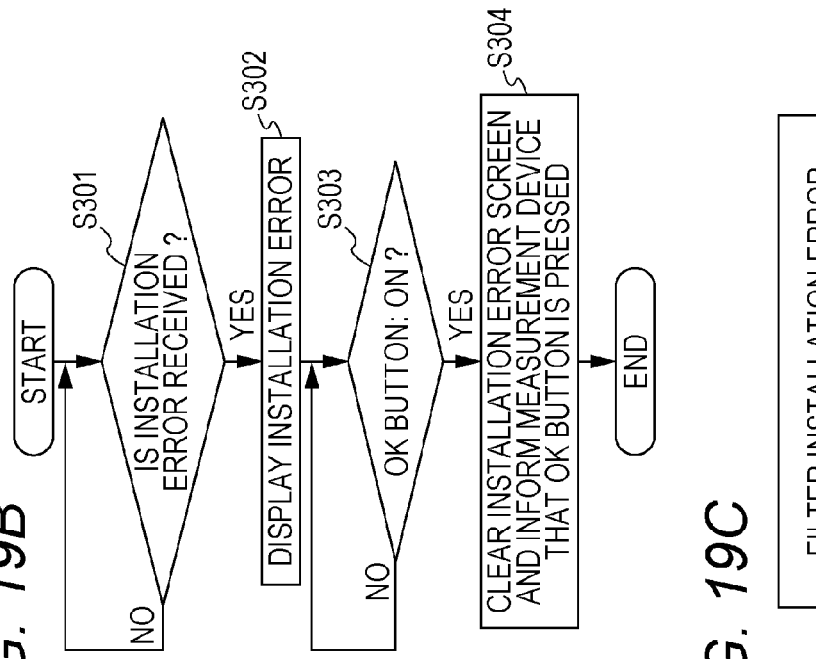
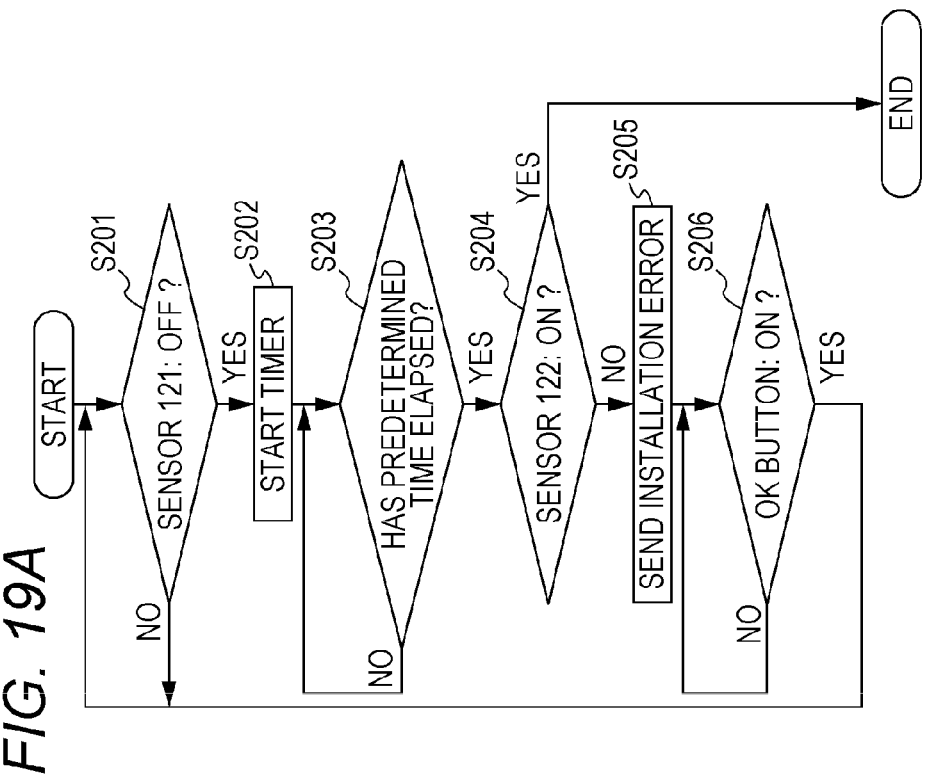

FILTER MEMBER AND A METHOD OF OBTAINING CELLS USING THE SAME

TECHNICAL FIELD

The present invention is related to a filter member and to a method for obtaining cells using the filter member.

BACKGROUND

Conventionally, a cell analyzer is known for analyzing cells contained in biological samples collected from a living body. For example, US Pub. No. 2008/108103 discloses a cell analyzer which determines the progression of canceration based on measurement results obtained by using a flow cytometer to measure epithelial cells contained in a sample collected from the cervix of a subject.

In this cell analyzer, it is preferable to use a large number of cells to be analyzed to increase the accuracy of analysis when performing analysis of individual cells. For example, US Pub. No. 2011/076755 discloses a sample preparation apparatus which is capable of increasing the number of cells per unit volume supplied for analysis by increasing the concentration of the cells contained in a sample.

This sample preparation apparatus has a storage chamber for accommodating a sample when the top surface is opened, a cylindrical piston which has a filter loaded at the bottom end surface and which is inserted into the storage chamber, a suction tube for suctioning a liquid that penetrates to the interior of the piston through the filter, and a stirrer disposed at the bottom of the storage chamber. In the process of concentrating the sample, the sample is first charged into the storage chamber. Thereafter, the piston is inserted in the storage chamber until the filter is immersed in the sample. At this time, the liquid leaking into the piston is suctioned by the suction tube and then removed from the storage chamber. The cells to be analyzed adhere to the bottom surface of the filter and do not pass through the filter. The cells adhered to the bottom surface of the filter are detached from the filter by operating the stirrer, if appropriate. The sample remaining in the storage chamber now contains a high concentration of cells to be analyzed.

In order to make replacement of the filter easy, it is contemplated that the filter is attached to a holding member, and then the member is detached from the apparatus.

SUMMARY OF THE INVENTION

The scope of the present invention is defined solely by the appended claims, and is not affected to any degree by the statements within this summary.

A first aspect of the present invention relates to a filter member. The filter member according to this aspect includes: a filter for discriminating cells to be analyzed in a sample from other components; a first filter holding member which comprises a first through hole and has a plate-like shape; and a second filter holding member which comprises a second through hole and is fitted into the first filter holding member. When the first and second filter holding members are integrated by fitting the second filter holding member into the first filter holding member, the filter is sandwiched between the first filter holding member and the second filter holding member, and the first through hole is opposed to the second through hole through the filter. A first elastic body is formed on a surface of the first filter holding member, the surface being in contact with the filter. A second elastic body is formed on a surface of the second filter holding member, the surface being in contact with the filter.

A second aspect of the present invention relates to a filter member. The filter member according to this aspect includes: a filter for discriminating epithelial cells in a sample from components smaller than the epithelial cells; a first filter holding member which comprises a first through hole and has a plate-like shape; and a second filter holding member which comprises a second through hole and is fitted into the first filter holding member. When the first and second filter holding members are integrated by fitting the second filter holding member into the first filter holding member, the filter is sandwiched between the first filter holding member and the second filter holding member and the first through hole is opposed to the second through hole through the filter. A first elastic body is formed on a surface of the first filter holding member, the surface being in contact with the filter. A second elastic body is formed on a surface of the second filter holding member, the surface being in contact with the filter.

A third aspect of the present invention relates to a method of obtaining cells using the filter member described in the first aspect. In the method of obtaining cells according to this aspect, the cells to be analyzed in the sample are discriminated from other components by passing the sample through the above filter, and the cells to be analyzed remaining on the above filter are obtained.

BRIEF DESCRIPTION OF DRAWINGS

FIGS. 7A to 7C are views showing the detailed structure of the filter member according to an embodiment;

FIGS. 8A to 8E are views showing the detailed structure of the filter member according to an embodiment;

FIGS. 9A and 9B are side and perspective views showing the structure of the piston according to an embodiment;

FIGS. 16A to 16I schematically show the container according to an embodiment and the condition of the liquid within the empty space;

FIGS. 17A to 17F are views showing the structure of the filter member according to a modified example;

FIGS. 19A and 19B are view showing the process and display examples when the filter member according to the modified example is installed incorrectly.

FIG. 19C shows an example of a display when the filter member is installed incorrectly.

DETAILED DESCRIPTION OF THE PREFERRED EMBODIMENTS

The preferred embodiments of the present invention will be described hereinafter with reference to the drawings.

The present embodiment is an embodiment in which the present invention is applied to a canceration information providing apparatus (cell analyzer) which prepares measurement samples containing cells (biological samples) collected from a subject, and obtains information relating to canceration of cells based on the prepared measurement samples. Hereinafter, a canceration information providing apparatus 1 according to the present embodiment will be described with reference to the drawings.

Figure 1:
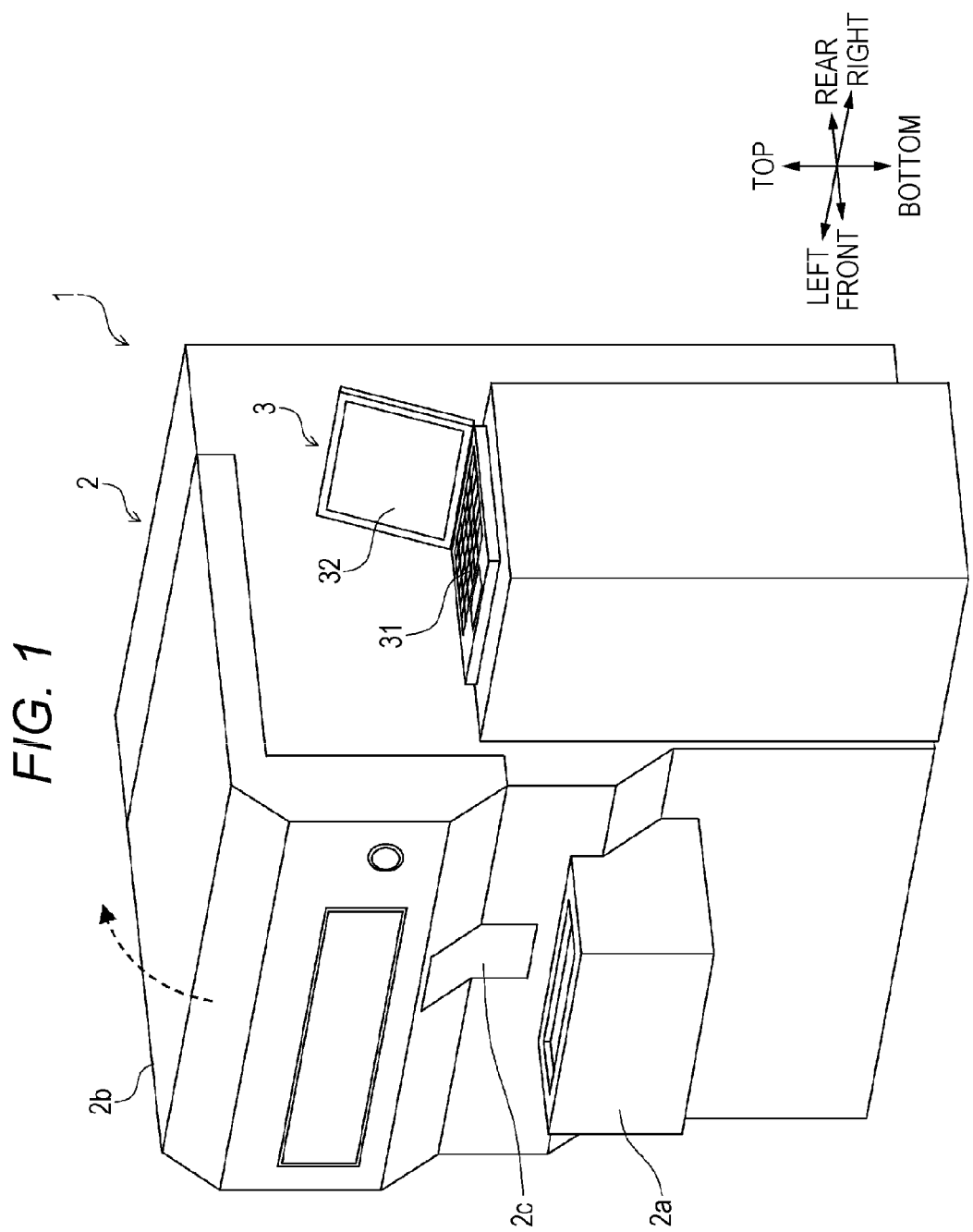
FIG. 1 is a perspective view showing an external view of the structure of a canceration information providing apparatus according to an embodiment.

FIG. 1 is a perspective view showing the structure of the canceration information providing apparatus 1.

The canceration information providing apparatus 1 comprises a measurement sample containing cells collected from a subject (hereinafter referred to as "cells to be analyzed") to flow through the flow cell, and irradiates the measurement sample with laser light as the sample flows through the flow cell. The light (forward scattered light, side scattered light and fluorescent light) from the measurement sample is then detected and the resulting optical signals are analyzed to determine whether the sample contains cancerous cells or cells in a process of becoming cancerous. Specifically, the canceration information providing apparatus 1 is used for screening cervical cancer using cervical epithelial cells collected from a subject.

The canceration information providing apparatus 1 comprises a measurement device 2 for performing measurements of cells to be analyzed and a data processing device 3 which is connected to the measurement device 2 and performs analyses of the measurement results. A sample receiver 2a capable of holding a plurality of sample containers 4 (refer to FIG. 2) is provided in front of the measurement device 2, and the sample container 4 contains a liquid mixture of cells collected from the cervix of a subject and a stock solution having methanol as a main component. The measurement device 2 is also provided with a cover 2b, and a user can access the interior of the measurement device 2 by lifting the cover 2b. The measurement device 2 is provided with an opening 2c for installing and removing a sample pipette unit 11 which is described later. The data processing device 3 includes an input unit 31 for receiving instructions from a user, and a display unit 32 for displaying the analysis results and the like.

Figure 2:
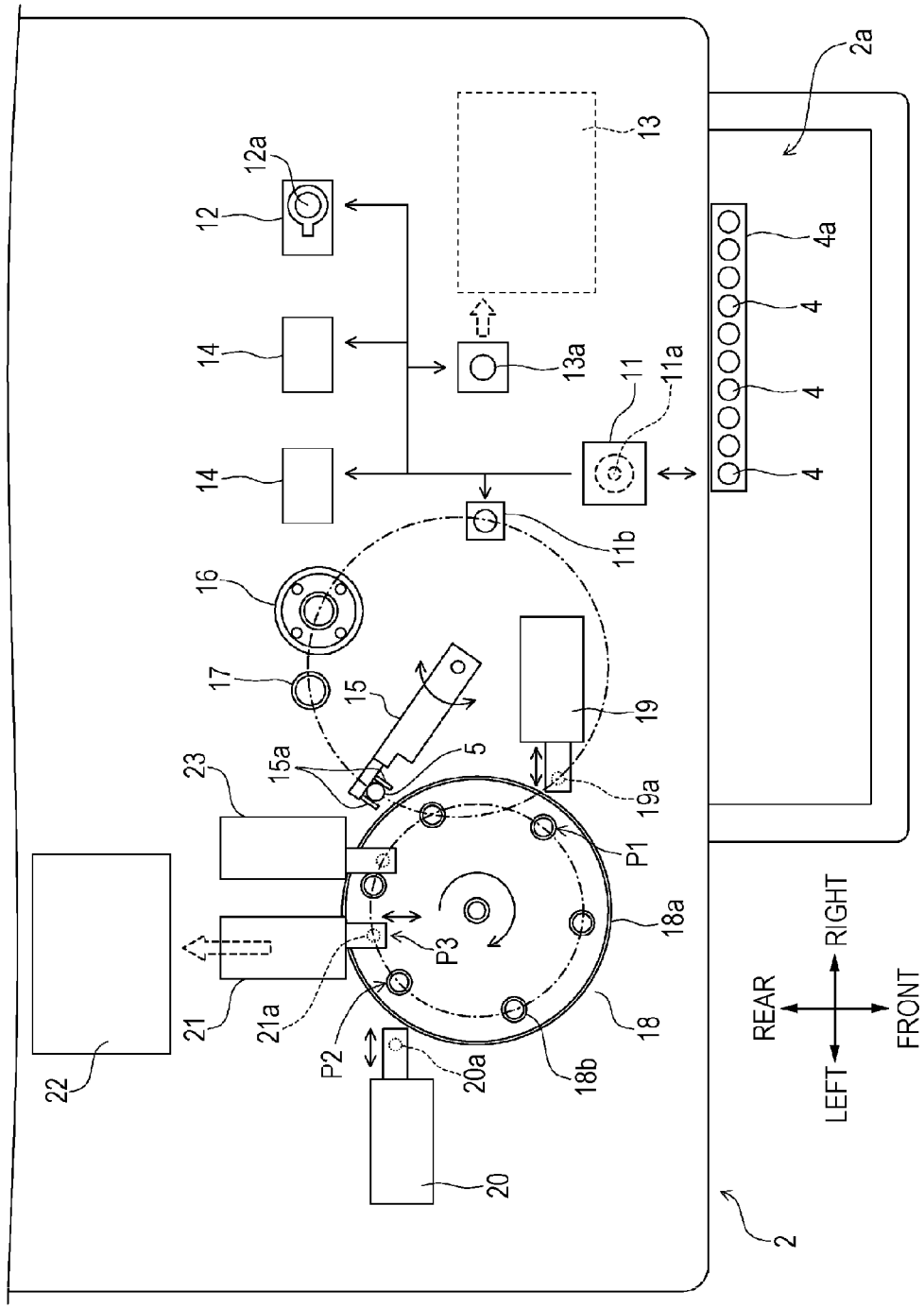
FIG. 2 is a plan view showing the internal structure of a measurement device according to the embodiment.

FIG. 2 is a plan view showing the internal structure of the measurement device 2.

The sample receiver 2a sequentially transports racks 4a which hold the sample containers 4 to the sample aspirating position of the sample pipette unit 11. The sample pipette unit 11 has a pipette 11a which extends in a vertical direction; the pipette 11a is configured to be movable in the vertical and horizontal directions to aspirate and discharge the sample.

When the sample container 4 is set at the aspirating position of the sample receiver 2a, the sample in the container 4 is aspirated by the sample pipette unit 11, and discharged into a sample receiving part 12a of a first dispersion unit 12. The first dispersion unit 12 disperses the aggregated cells contained in the sample by applying a shearing force. The sample which has been processed (first dispersion process) by the first dispersion unit 12 is then aspirated by the sample pipette unit 11 and discharged into a sample capture unit 13a of a sub detection unit 13. The sub detection unit 13 has a flow cytometer which measures the concentration of the sample by detecting (pre-measurement) the number of cells to be analyzed. The amount of the sample to be aspirated for the main measurement by the main detection unit 22 is determined based on the concentration measurement.

The sample in the sample receiving part 12a of the first dispersion unit 12 is aspirated by the sample pipette unit 11 in the amount determined above, and the aspirated sample is then discharged in a receiving part 210 (refer to FIG. 5A) of a discrimination/replacement unit 14. Two discrimination/replacement units 14 are provided to perform processing in parallel.

The discrimination/replacement unit 14 replaces the stock solution having a main component of methanol in the sample with diluent. That is, the discrimination/replacement unit 14 performs processing to dilute the concentration of the methanol in the sample using the diluent so as to appropriately perform the cell staining process in the next process. Tris-HCL (buffer) is used as the diluent. The discrimination/replacement unit 14 also discriminates the cells to be analyzed (cervical epithelial cells) from other components (erythrocytes, leukocytes, bacteria and the like) and foreign substances in the sample. Thus, a concentrated liquid of cells to be analyzed is obtained, which contains the number of cells required for cancer cell detection. Details of the structure of the discrimination/replacement unit 14 will be described later.

Then, the measurement sample container 5 arranged in a retainer 18b of a reactor 18 is grasped by a tapered holder 15a of a container transporter 15 and positioned at a sample transfer part 11b. The concentrate in the receiving part 210 of the discrimination/replacement unit 14 is then aspirated by the sample pipette unit 11, and discharged into the measurement sample container 5 positioned in the sample transfer part 11b. The container transporter 15 moves the measurement sample container 5 to a second dispersion unit 16.

The second dispersion unit 16 applies ultrasonic waves to the concentrated sample in the discrimination/replacement unit 14. Hence, the aggregated cells remaining after the first dispersion process are dispersed into single cells. After processing by the second dispersion unit 16 (second dispersion process), the measurement sample container 5 is moved to a liquid removal unit 17 by the container transporter 15. The liquid removal unit 17 removes the liquid component (moisture reduction) adhered to the outer surface of the measurement sample container 5. After processing by the liquid removal unit 17, the measurement sample container 5 is moved to the retainer 18b of the reactor 18 by the container transporter 15.

The reactor 18 heats the measurement sample container 5 held in the retainer 18b to a predetermined temperature (approximately 37 degrees) to promote a reaction between the sample in the measurement sample container 5 and a reagent added by a first reagent adding unit 19 and a second reagent adding unit 20. The reactor 18 has a rotatable circular table 18a, and a plurality of retainers 18b are provided along the circumference of the rotating table 18a to receive measurement sample containers 5.

The first reagent adding unit 19 and the second reagent adding unit 20 have suppliers 19a and 20a, respectively, which are movable to positions P1 and P2, respectively, above the measurement sample container 5 disposed on the rotating table 18a. The first reagent adding unit 19 and the second reagent adding unit 20 add a predetermined amount of reagent from the supplier 19a or 20a into the measurement sample container 5 when the measurement sample container 5 is moved to the position P1 or P2 via the rotating table 18a.

The reagent added by the first reagent adding unit 19 is RNase which is used for RNA removal, and the reagent added by the second reagent adding unit 20 is a stain used for DNA staining. RNA removal processing degrades the RNA in cells to allow for measurement of only the DNA. The DNA staining process is performed using propidium iodide (PI), which is a fluorescent stain containing pigment. The DNA staining process selectively stains the nucleus in the cell. Hence, fluorescent light from the nucleus can be detected.

A sample aspirator 21 has a pipette 21a which is movable to a position P3 above the measurement sample container 5 on the rotating table 18a, and the sample aspirator 21 aspirates the sample in the measurement sample container 5 when the measurement sample container 5 has been transported to the position P3 by the rotating table 18a. The sample aspirator 21 is connected to the flow cell of the main detection unit 22 through a flow path which is not shown in the drawing, and supplies the measurement sample aspirated by the pipette 21a to the flow cell of the main detection unit 22.

The main detection unit 22 has a flow cytometer for detecting light (forward scattered light, side scattered light, fluorescent light) from the measurement sample, and outputs signals based on each type of light to circuits which are described later. A container washing unit 23 washes the interior of the measurement sample container 5 after the measurement sample has been supplied to the main detection unit 22 by the sample aspirator 21 by discharging washing liquid into the measurement sample container 5 disposed on the rotating table 18a.

Figure 3:
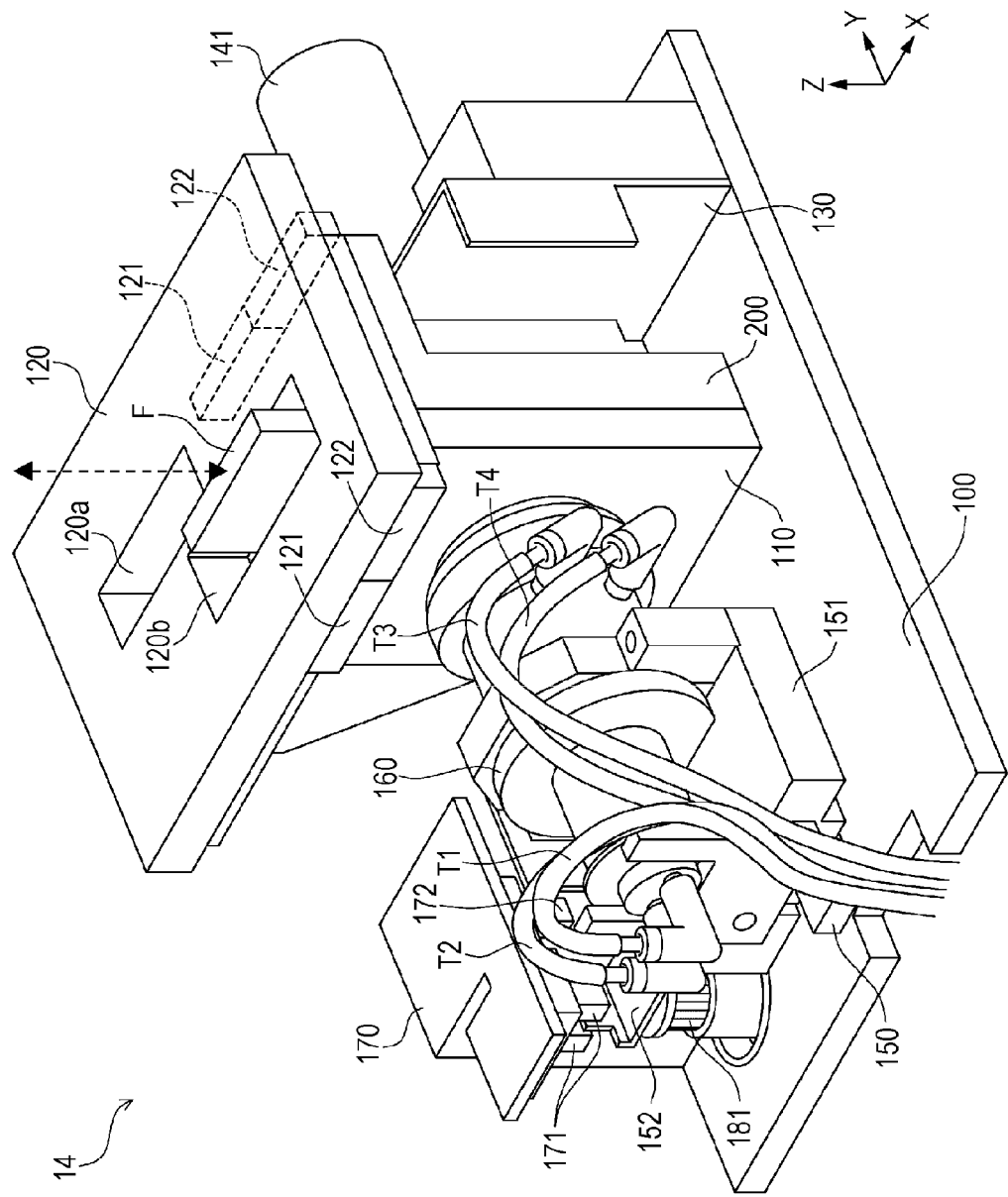
FIG. 3 is a perspective view showing the structure of a discrimination/replacement unit according to an embodiment.

FIG. 3 is a perspective view showing the structure of the discrimination/replacement unit 14. In FIG. 3, the Z axis direction is vertical, and the Z axis positive direction and Z axis negative direction are the upward direction and downward direction, respectively.

A base 100 is a plate-like member parallel to the XY plane. A container body 200, support members 110, 130, 170, and a rail 150 are provided on the base 100. Note that various mechanisms are also provided on the base 100. These various mechanisms are omitted in FIG. 3 for clarity.

The support member 110 is a plate-like member parallel to the XZ plane. The support member 110 has a hole 111 (refer to FIG. 10) formed therein which passes through in the Y axis direction. A top plate 120 is provided on the top surface of the container body 200 and the support member 110. The top plate 120 is positioned within the measurement device 2 so as to allow the user to access the top plate 120 when the cover 2b (refer to FIG. 1) of the measurement device 2 is opened upward.

The top plate 120 has through holes 120a and 120b in the vertical direction. The pipette 11a of the sample pipette unit 11 aspirates and discharges a sample from/to the receiving part 210 of the container body 200 (described later) through the hole 120a. The user opens the cover 2b of the measurement device 2, and installs and removes a filter member F in a receiving part 220 of the container body 200 (described later) through the hole 120b along the dashed arrow (vertical direction).

The top plate 120 is a translucent member. Sensors 121 and 122 which are configured by light emitters and light receivers are provided on the top plate 120. When the filter member F is properly installed, light emitted from the light emitter of the sensor 121 is blocked by the filter member F. The light emitted from the light emitter of the sensor 122 passes through a slot F6 (refer to FIGS. 6A and 6B) of the filter member F. When the filter member F is installed with the surfaces F1 and F2 (refer to FIGS. 6A and 6B) of the filter member F facing opposite directions, the light emitted from the light emitter of the sensors 121 and 122 is blocked by the filter member F. The proper installation of the filter member F thus can be determined.

The support member 130 supports a motor 141. A support member 151 is arranged on the rail 150 so as to be slidable in the Y axis direction. A flange 152 and a piston 160 are provided on the support member 151. Tubes T1 to T4 are connected to the piston 160. Sensors 171 and 172 which are configured by light emitters and light receivers are provided on the support member 170.

Figure 4A:
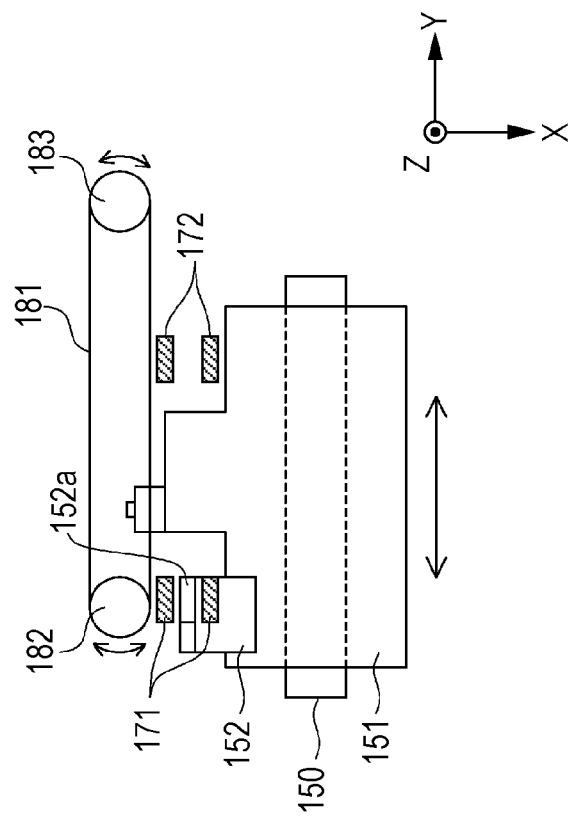
FIG. 4A is a side view of the motor according to an embodiment and FIG. 4B is a plan view showing the mechanism for driving a piston viewed from above.

FIG. 4A is a side view of the motor 141. The rotational axis of the motor 141 is parallel to the Y axis, and matches the center axis A which is described later. A magnet 142 is attached to the tip of the motor 141 in the Y axis negative direction. A stirrer R which is described later is rotated through the wall of the container body 200 by driving the motor 141 to rotate the magnet 142 in the XZ plane.

Figure 4B:
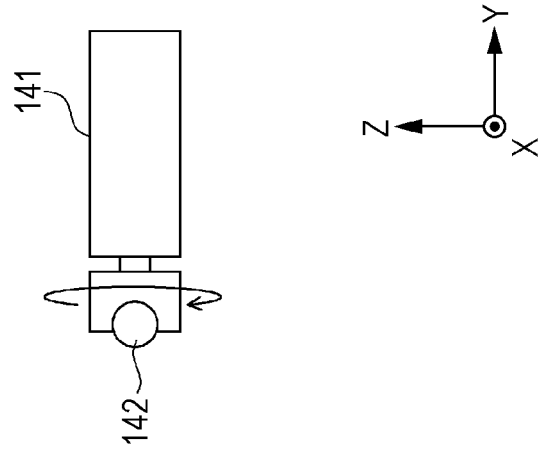

FIG. 4B is a plan view illustrating the mechanism for driving the piston 160 viewed from above. The illustration of the piston 160 in FIG. 4B is omitted for convenience. The support member 151 is attached to a belt 181. The belt 181 is supported by pulleys 182 and 183. The pulley 182 is connected to the rotational shaft of a step motor mounted on the bottom surface side of the base 100. When the step motor is driven, the support member 151 is slid on the rail 150 in the Y axis direction, and the piston 160 is driven in the Y axis direction. The sensors 171 and 172 are positioned to detect a shield 152a of the flange 152 provided on the support member 151. The piston 160 positioned on the leftmost side and positioned on the rightmost side can be detected by the detection signals of the sensors 171 and 172.

Figures 5A, 5B, 5C:
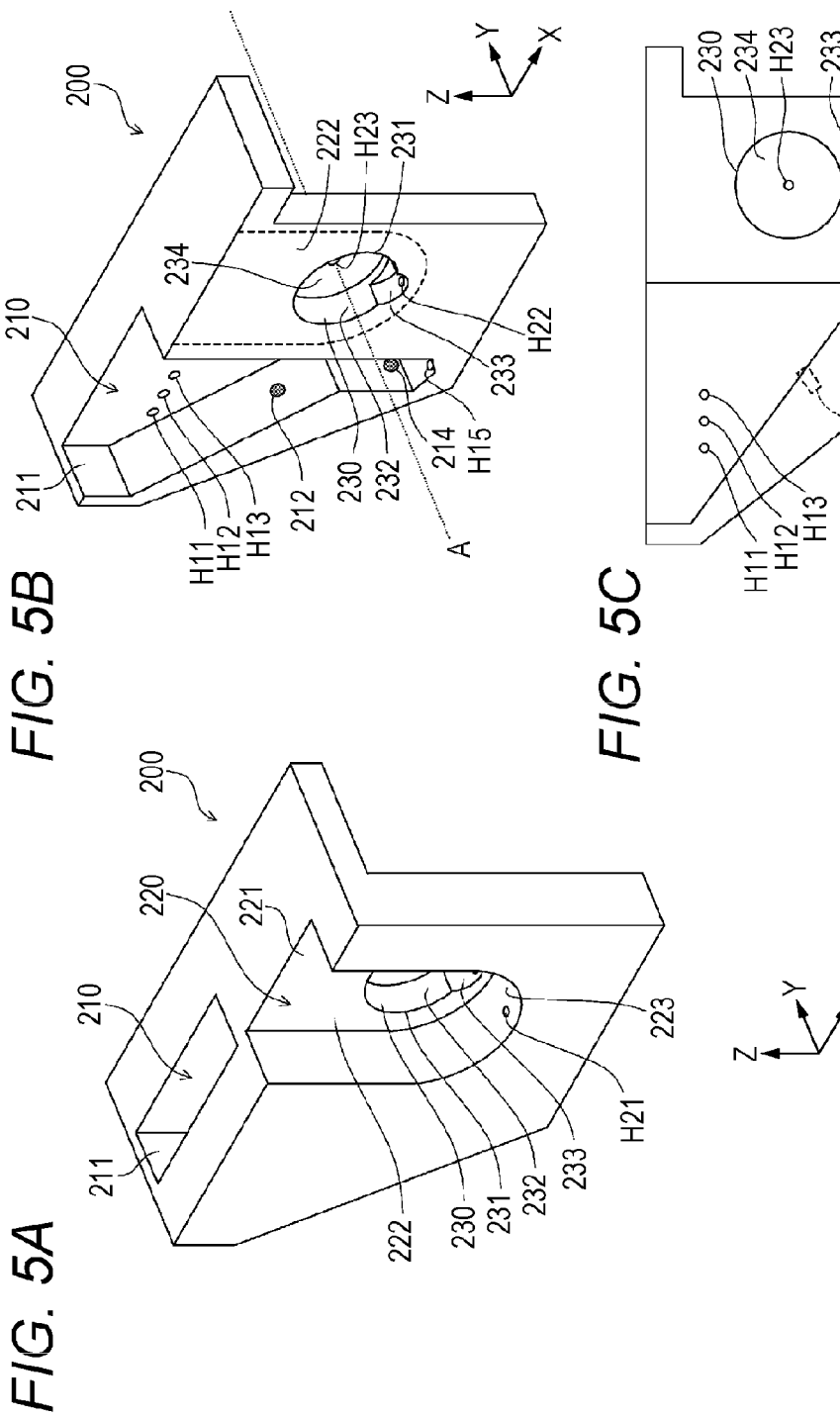
FIG. 5A is a perspective view showing the structure of a container body according to an embodiment.
FIGS. 5B and 5C are perspective and side views of the container body cross section.

FIG. 5A is a perspective view showing the structure of the container body 200. FIG. 5B is a perspective view of the cross section of the container body 200 on the plane that includes a wall 222 in FIG. 5A. FIG. 5C is a side view of the container body 200 shown in FIG. 5B viewed in the Y axis positive direction.

Referring to FIG. 5A, receiving parts 210 and 220 are formed in the container body 200. An insertion port 211 is positioned at the top part of the receiving part 210, and is linked to the hole 120a of the top plate 120. An insertion port 221 is positioned at the top part of the receiving part 220, and is linked to the hole 120b of the top plate 120. The receiving part 220 has the wall 222 parallel to the XZ plane, and a concavity 230 for accommodating the stirrer R (described later) is formed in the wall 222. A bottom surface 223 of the receiving part 220 is curved. A hole H21 is formed at the lowest position of the bottom surface 223. The side of the receiving part 220 is opened in the Y axis negative direction.

Referring to FIGS. 5B and 5C, the concavity 230 has an opening 231 which opens the concavity 230 on the Y axis negative direction side, a circular inner surface 232 viewed in the Y axis direction, a reservoir 233 formed below the inner surface 232, and a wall 234 parallel to the XZ plane. The concavity 230 is separated from the container part 210 in planar view, that is, in the direction within the XY plane (horizontal direction). The center axis A indicated by the dotted line in FIG. 5B is an axis which passes through the center of the circular shape when the inner surface 232 is viewed in the Y axis direction and which is parallel to the Y axis direction. The reservoir 233 is formed as a concavity in a direction from the center axis A on the inner surface 232. A hole H22 is formed at the lowest position of the reservoir 233. A hole H23 is formed in the wall 234 at a position at which the center axis A intersects the wall 234.

The receiving part 210 is shaped so that the inner part gradually becomes narrower in the depth direction (downward direction). Holes H11 to H13 are formed in the top part of the inner surface of the receiving part 210. Holes H14 and H15 are formed in the innermost part of the receiving part 210. The hole H14 is linked through a flow path 241 to the hole H22 of the reservoir 233. The hole H15 is linked through a flow path 242 to a hole H16 formed in the outer surface of the container body 200. The disposition of the receiving part 210, concavity 230, and flow path 241 are adjusted so that the hole H14 is lower than the hole H22. Note that the hole H16 is connected to a valve V25 (refer to FIG. 12), and the diameter of the flow path 242 is sufficiently small. Therefore, the sample held in the receiving part 210 does not flow downward from the hole H15.

Pins 212 to 214 are provided in the receiving part 210. The pins 212 to 214 are connected to a resistance type liquid surface sensor 293 (refer to FIG. 13). The liquid surface sensor 293 detects whether the surface of the liquid in the receiving part 210 is above the height of the position of the pin 212 based on the state of the current flow of the pins 212 and 214. The liquid surface sensor 293 detects whether the surface of the liquid in the receiving part 210 is above the height of the position of the top part of the pin 213 based on the current flow of the pins 213 and 214.

Figure 6A:
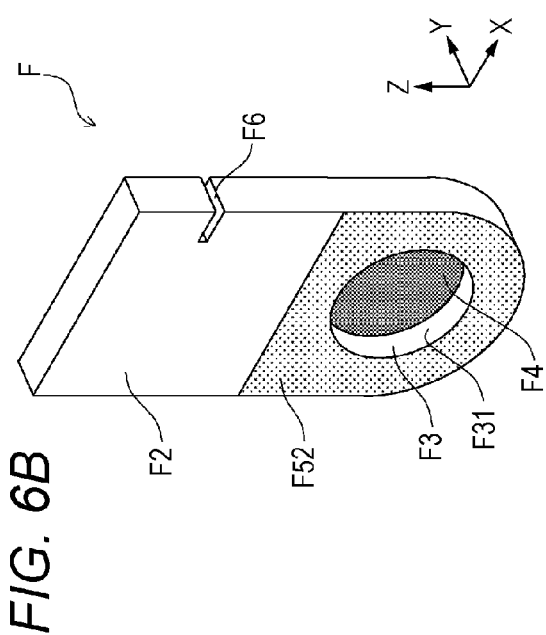
FIGS. 6A and 6B are perspective views showing the structure of a filter member according to an embodiment.
Figure 6B:
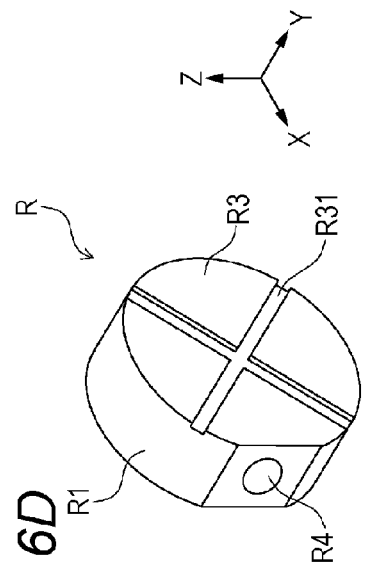

FIGS. 6A and 6B are perspective views showing the structure of the filter member F. FIGS. 6A and 6B show the coordinate axes of the properly placed filter member F relative to the receiving part 220.

The filter member F has surfaces F1 and F2 parallel to the XZ plane, holes F3 passing through the filter member F in the Y axis direction, filter F4, thin film rubber F51 installed on the surface F1, and thin film rubber F52 installed on the surface F2. Surfaces F1 and F2 are positioned on the Y axis positive direction side and the Y axis negative direction side, respectively. The hole F3 has a cylindrical inner surface F31.

The filter F4 is installed so that the filter surface is parallel to the XZ plane relative to the inner surface F31 of the hole F3. The filter F4 is porous and has pores of a certain diameter such that components (erythrocytes, leukocytes, bacteria, foreign substances) which have a diameter smaller than cells to be analyzed (cervical epithelial cells) pass through the filter F4, whereas cells to be analyzed cannot pass through.

The size of the cervical epithelial cells is from about 20 to 80 μm (average size: about 60 μm). The size of erythrocytes which are cells smaller than the cells to be measured is from about 7 to 10 μm. The size of leukocytes which are cells smaller than the cells to be measured is from about 8 to 15 μm. The size of foreign substances such as bacteria is from about 1 to several μm.

The filter F4 of the present embodiment is made of metal and has holes having a diameter of 8 μm or more and less than 20 μm such that epithelial cells do not pass through the holes of the filter F4. When the diameter of the holes is less than 8 μm, there is often a phenomenon that cells and foreign substances are aggregated in the holes, whereas when the diameter of the holes is 20 μm or more, epithelial cells may pass through the holes of the filter F4. Preferably, the diameter of the hole of the filter F4 is around 10 μm.

The filter may be produced by any known method such as Electro-Fine-Forming or Chemical Vapor Deposition (CVD).

The distance between the filter F4 and the surface F1 in the Y axis direction is less than the distance between the filter F4 and the surface F2. The rubber F51 is installed around the circumference of the opening of the hole F3 on the surface F1 side, and the surface F11 which is part of the surface F1 is exposed between the rubber F51 and the opening of the hole F3 on the surface F1 side. The rubber F52 is installed around the circumference of the opening of the hole F3 on the surface F2 side. Describing in more details, the filter member F shown in FIGS. 6A and 6B is configured as shown in FIGS. 7A to 8E. Hereinafter, the detailed structure of the filter member F will be described with reference to FIGS. 7A to 8E.

FIG. 7A is an exploded view of the filter member F, FIG. 7B shows the structure of the end in the Z axis negative direction side of a holding member F100, and FIG. 7C shows the structure of a holding member F200. FIGS. 8A and 8B show that the filter F4 is sandwiched between the holding members F100 and F200, and FIGS. 8C and 8D are views of the completed filter member F. FIG. 8E is a cross-sectional view of the filter member F on the plane inclined at 45 degrees to the X and Z axes.

As shown in FIG. 7A, the filter member F is configured by a plate-like holding member F100, a circular holding member F200, a circular-shaped filter F4, and ring-shaped rubbers F51 and 52. As shown in FIGS. 7A and 7B, a concavity F110 having a surface F111 which is one step lower than the peripheral surface is formed on the Y axis negative direction side below the holding member F100 (Z axis negative direction side). A hole F120 passing through the holding member F100 in the Y axis direction is formed in the center of the surface F111. The hole F120 has a cylindrical inner surface F121. Four holes F130 passing through the holding member F100 in the Y axis direction are formed in the circumference of the surface F111.

As shown in FIGS. 7B and 8E, the surface on the circumference side of the hole F130 is dented outward from the inner wall of the concavity F110. Thus, level differences are formed on the inner wall of the concavity F110, and the level differences serve as engaging parts F131 which engage with retainers F231 (described later). Note that the hole F130 passes from the concavity F110 to the rear surface of the holding member F100. This is because a metal mold part for forming the engaging part F131 is pulled in the Y axis positive direction when molding the holding member F100. That is, the hole F130 thus passes to the rear surface of the holding member F100 so that the engaging part F131 can be formed easily.

As shown in FIGS. 7A and 7B, an elastic body F140 is molded around the circumference in the Y axis negative direction side of the hole F120 by two-color molding. The top surface of the elastic body F140 is one step lower than the surface F111. The diameter of the circumference of the elastic body F140 is substantially the same as that of the filter F4. Thus, the position of the filter F4 is determined by installing the filter F4 on the elastic body F140, during the assembly of the filter member F.

As shown in FIG. 8A, a circular-shaped surface F151 is formed on the circumference on the Y axis positive direction side of the hole F120, and a surface F152 which is one step lower than the surface F151 is formed on the circumference of the surface F151. The diameter of the circumference of the surface F151 is substantially the same as that of a hole F51a of the rubber F51. Thus, the position of the rubber F51 is determined by installing the rubber F51 on the surface F152, during the assembly of the filter member F.

As shown in FIGS. 7A and 8A, a surface F101 which is one step lower than the peripheral surface is formed on the holding member F100. Thus, in the holding member F100, the thickness near a top edge F102 in the Z axis positive direction (longitudinal direction) away from the position to which the filter F4 is attached is larger than the thickness of the surface F101 on the longitudinally inner side (Z axis negative direction side). When the filter member F is attached to the receiving part 220, the top part of the filter member F as well as the top edge F102 are configured to protrude into the top part of the hole 120b of the top plate 120 as shown in FIG. 3. Note that the slot F6 passing through the holding member F100 in the Y axis direction is formed in the end on the X axis positive direction side of the holding member F100 as described above.

As shown in FIGS. 7A and 7C, a surface F210 parallel to the XZ plane is formed on the Y axis negative direction side of the holding member F200. A circular hole F220 passing through the holding member F200 in the Y axis direction is formed in the center of the surface F210. The hole F220 has a cylindrical inner surface F221. The diameter of the hole F220 is substantially the same as that of a hole F52a of the rubber F52. Four protruding parts F230 are formed on the Y axis positive side of the holding member F200. Retainers F231 protruding around the circumference are formed at the tip of each of the protruding parts F230.

An elastic body F240 is molded around the circumference in the Y axis positive direction side of the hole F220 by two-color molding. The top surface of the elastic body F240 is one step higher than the peripheral surface of the elastic body F240. The diameter of the circumference of the elastic body F240 is substantially the same as that of the filter F4.

As shown in FIG. 7A, the filter F4 is configured by a central part F41 and a thick part F42. As described above, the central part F41 has pores of a certain diameter such that components (erythrocytes, leukocytes, bacteria, foreign substances) which have a diameter smaller than cells to be analyzed (cervical epithelial cells) pass through the filter F4, whereas cells to be analyzed cannot pass through. The thickness of the central part F41 is about 10 µm. The thick part F42 is formed by subjecting the circumference of the central part F41 to electroforming. The thickness of the thick part F42 is configured to be larger than that of the central part F41, and it is about 0.1 mm.

The holes F51a and F52a are formed in the centers of the rubbers F51 and F52, respectively. The diameter of the circumference of the rubber F51 and the diameter of the circumference of the rubber F52 are substantially the same as the diameter of the circumference of the surface F152 of the holding member F100 and the diameter of the circumference of the holding member F200, respectively.

When the filter member F is assembled, the filter F4 is first installed on the elastic body F140 of the holding member F100. At this time, the thick part F42 of the filter F4 is in contact with the elastic body F140. Then, the holding member F200 is fitted into the concavity F110 of the holding member F100 such that the protruding part F230 of the holding member F200 faces the hole F130 of the holding member F100. At this time, the protruding part F230 abuts the inner wall of the concavity F110 and undergoes an elastic deformation inward. Thereafter, when the retainer F231 of the protruding part F230 reaches the position of the engaging part F131, the protruding part F230 undergoes an elastic recovery outward and the retainer F231 is engaged with the engaging part F131 as shown in FIG. 8E. Thus, the thick part F42 of the filter F4 is sandwiched between the elastic bodies F140 and F240. As shown in FIGS. 8A and 8B, the filter F4 is thus sandwiched between the holding members F100 and F200.

Then, the rubber F51 is stuck to the surface F152 of the holding member F100 with double-sided tape, and the rubber F52 is stuck to the surface F210 of the holding member F200 with double-sided tape. As show in FIGS. 8C and 8D, the filter member F is thus completed.

Note that the surface F11 in FIGS. 6A and 6B corresponds to the surface F151 of the holding member F200. The hole F3 is configured by the hole F120 of the holding member F100 and the hole F220 of the holding member F200. The inner surface F31 is configured by the inner surface F121 of the holding member F100 and the inner surface F221 of the holding member F200. Hereinafter, for convenience of illustration, the present invention will be described using the filter member F shown in FIGS. 6A and 6B.

Figure 6C:
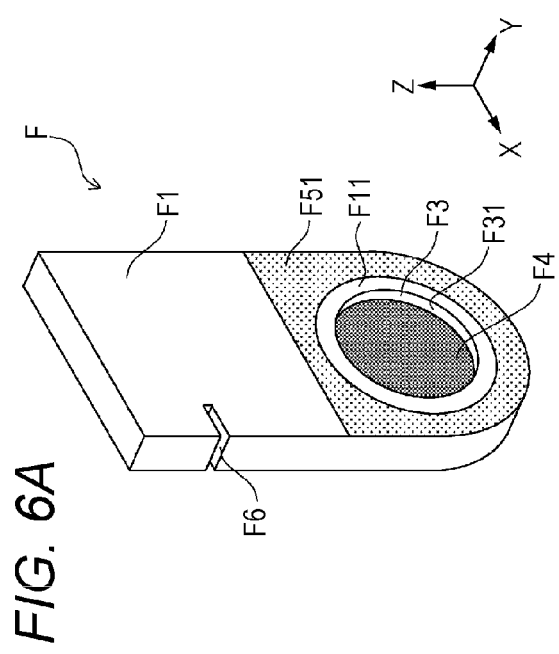
FIGS. 6C and 6D are perspective views showing the structure of a stirrer.
Figure 6D:
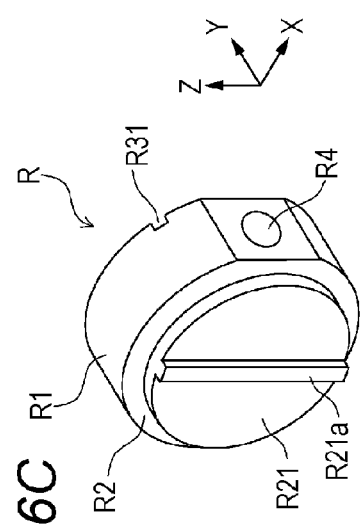

FIGS. 6C and 6D are perspective views showing the structure of the stirrer R. FIGS. 6C and 6D show the coordinate axes of the stirrer R accommodated in the concavity 230.

The stirrer R has a body R1, surfaces R2 and R3 parallel to the XZ plane, and a magnet R4. The surfaces R2 and R3 are positioned on the Y axis negative direction side and the Y axis positive direction side, respectively. A convexity R21 which protrudes from the surface R2 in the Y axis negative direction side is formed on the surface R2. The diameter of the convexity R21 is smaller than the diameter of the circumference of the surface R2. A flange R21a is formed on the concavity R21. A channel R31 is formed to intersect the center of the surface R3. The magnet R4 is arranged to pass through the stirrer R within the XZ plane through the center of the stirrer R. Thus, the stirrer R rotates on the Y axis when a motor 141 rotates the magnet 142 shown in FIG. 4A.

FIGS. 9A and 9B are side and perspective views showing the structure of the piston 160.

The piston 160 has a rod-like tip 161 in the Y axis positive direction side. The tip 161 on the Y axis positive direction side has a concavity 162, an opening 163 which opens the concavity 162 in the Y axis positive direction, and a surface 164. Holes H31 to H34 are formed on the surface of the concavity 162 on the Y axis negative direction side. The holes H31 to H34 are respectively connected to the tubes T1 to T4 through a flow path provided inside the piston 160. An L-shaped pipe 165 is connected to the hole H31. The tip of the pipe 165 is positioned at the top part (the side in the Z axis positive direction) inside the concavity 162. The surface 164 is parallel to the XZ plane and is formed on the periphery of the opening 163.

Figure 10:
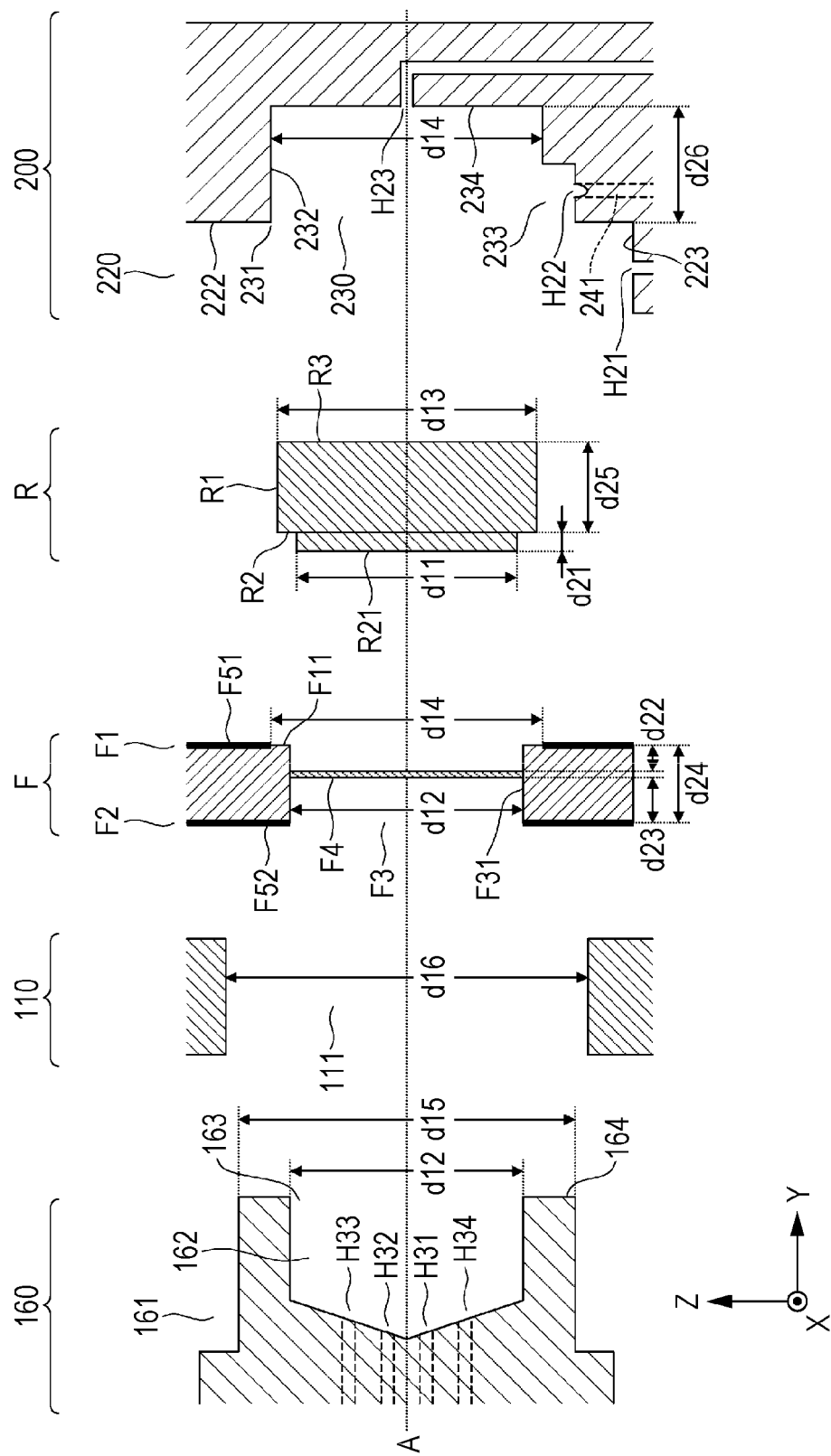
FIG. 10 is a cross-sectional view showing a piston, a support plate, a filter member, a stirrer, and a container body viewed through the center of axis plane.

FIG. 10 is a cross sectional view of the piston 160, support member 110, filter member F, stirrer R, and container body 200 viewed on the YZ plane through the center axis A. FIG. 10 conventionally shows the spacing of each part in the Y axis direction. Reference numbers d11 to d16 indicate the length in the Z axis direction, and the values increase in this sequence. Reference numbers d21 to d26 indicate the length in the Y axis direction, and the values increase in this sequence.

The concavity 162 in the piston 160 has a diameter d12, and the circumference of the surface 164 has a diameter d15. The hole 111 in the support member 110 has a diameter d16. The hole F3 in the filter member F has a diameter d12. The circumference of the surface F11 has a diameter d14. The distance between the surface F1 and the filter F4 is d22. The distance between the surface F2 and the filter F4 is d23. The distance between surfaces F1 and F2 is d24. The body R1 in the stirrer R has a diameter d13. The convexity R21 has a diameter d11. The body R1 has a width d25. The convexity R21 including the flange R21a has a width d21. The internal surface 232 in the container body 200 has a diameter d14. The concavity 230 has a diameter d26.

Note that in the condition of the filter member F shown in FIGS. 7A to 8E, the holes F120 and F220 have a diameter d12, the circumference of the surface F151 has a diameter d14 (the diameter of the hole F51a of the rubber F51), the distance between the surface F151 and the filter F4 is d22, the distance between the top surface of the rubber F52 and the filter F4 is d23, and the distance between the top surface of the rubber F51 and the top surface of the rubber F52 is d24.

Note that the concavity 162, the circumference of the surface 164, the holes 111 and F3, the circumference of the surface F11, the body R1, the convexity R21, and the concavity 230 are circular when viewed from the Y axis direction. The center of the circular shapes coincides with the center axis A.

FIGS. 11A to 11D show the sequence of the installation of the filter member F in the receiving part 220. FIGS. 11A to 11D are cross-sectional views similar to FIG. 10.

FIG. 11A shows the condition when the filter member F is not installed in the receiving part 220. The piston 160 is prepositioned at the leftmost side at this time, and the surface R3 of the stirrer R pulled further to the rightward direction by the magnet 142 (refer to FIG. 4A) and grounded at the wall 234. When the filter member F is inserted into the receiving part 220 through the hole 120b of the top plate 120 and the insertion opening 221 of the receiving part 220, the condition changes from that shown in FIG. 11A to the condition shown in FIG. 11B. The filter member F is supported in the upward direction by the bottom surface 223 of the receiving part 220.

When the piston 160 is positioned on the rightmost side as shown in FIG. 11B, the surface 164 of the piston 160 presses against the rubber F52 of the filter member F, and the rubber F51 of the filter member F presses against the wall 222 of the receiving part 220 as shown in FIG. 11C. Hence, the concavity 230 and the concavity 162 are combined through the filter F4. At this time, a space S1 which is closed to the outside is formed by blocking the opening 231 of the concavity 230 via the filter member F. A space S2 which is closed to the outside is also formed by blocking the opening 163 of the concavity 162 via the filter member F.

Specifically, the space S1 is formed by the side surface of the filter F4 on the concavity 230 side, the inner surface F31, the surface F11, the rubber F51, the inner surface 232, the reservoir 233, and the wall 234. The space S1 is structurally linked to the outside at this time through the holes H22 and H23. During the discrimination/replacement process, however, the hole H22 is actually closed because the sample is stored in the deepest part of the receiving part 210 positioned at the bottom end of the flow path 241 linked to the hole H22. The valve V24 (refer to FIG. 12), which is configured to be capable of closing the flow path is installed in the flow path linked to the hole H23, and the hole H23 is actually closed due to the diluent flowing through the hole H23 from the outside into the space S1. Thus, the space S1 is closed to the outside.

As described above, the filter F4 has pores of a diameter which allows cells having a size smaller than that of the cells to be analyzed to pass through, but does not allow the cells to be analyzed to pass through. Therefore, cells smaller than the cells to be analyzed in the space S1 pass through the filter F4, and the cells to be analyzed in the space S1 remain in the space S1.

Specifically, the space S2 is formed by the side surface of the filter F4 opposite the concavity 230, the inner surface F31, the rubber F52, and the concavity 162. The space S2 is structurally linked to the outside at this time through the holes H31 to H34. The holes H31 to H34 are actually closed because a value capable of closing the flow path is installed in the flow path linked to the holes H31 to H34. Thus, the space S2 is closed to the outside.

In the condition shown in FIG. 11C, the stirrer R rotates along the side surface (filtration surface) of the filter F4 on the concavity 230 side centered on the center axis A by rotating the magnet 142 (refer to FIG. 4A). At this time, a channel R31 is formed in the flat surface R3 of the stirrer R as shown in FIG. 6D. Therefore, the diluent smoothly flows into the space S1 from the hole H23.

The stirrer R separates from the wall 234 and moves toward the filter member F as shown in FIG. 11D when rotating by the magnet 142. As shown in FIG. 10, however, the width d21 of the convexity R21 which includes the flange R21a is smaller than the distance d22 between the surface F11 and the filter F4. The diameter d11 of the convexity R21 is smaller than the diameter d14 of the hole F3. The circumference (diameter of the body R1) d13 of the surface R2 is larger than the diameter d14 of the hole F3. Therefore, the convexity R21 including the flange R21a abuts the filter F4 whereby damage to the filter F4 is prevented by the surface R2 abutting the surface F11 as shown in FIG. 11D.

Figure 12:
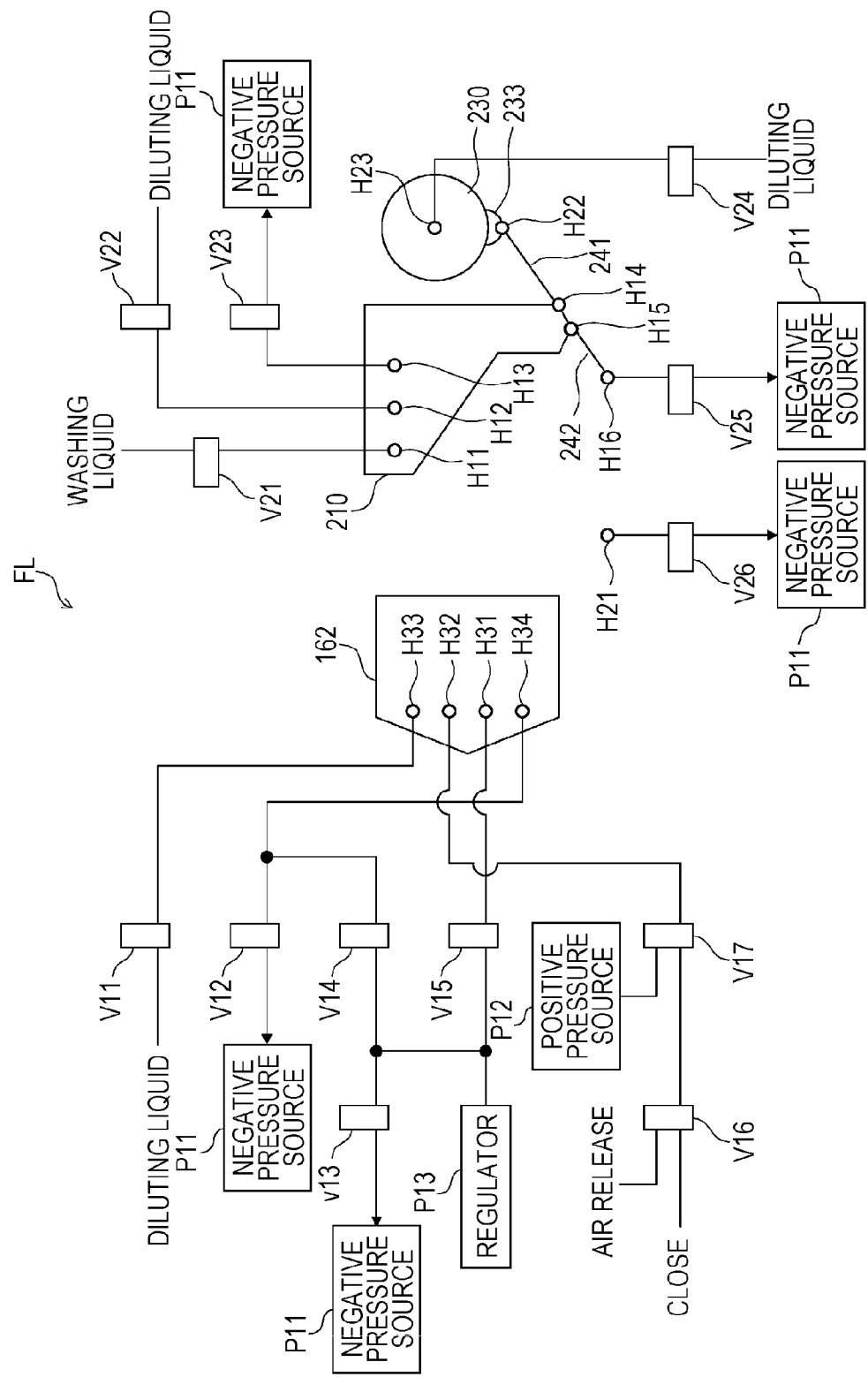
FIG. 12 is a view showing the fluid processing unit of the measurement device according to the embodiment.

FIG. 12 shows a fluid processing unit FL of the measurement device 2.

Valves V11 to V15 and V21 to V26 are configured to switch between a state to open the flow path and a state to close the flow path. Valves V16 and V17 are configured to connect to any flow path connected on the left side relative to one flow path on the right side. The holes H31 to H34 are respectively connected to the valves V15, V17, V11, V12, and V14. The holes H11 to H13 are respectively connected to the valves V21 to V23. The holes H23, H16, and H21 are respectively connected to the valves V24, V25, and V26. A negative pressure source P11 is connected to valves V12, V13, V23, V25, and V26, and a positive pressure source P12 is connected to valve V17. A regulator P13 is connected to the valves V13 through V15 to regularize the pressure. The driving of the fluid processing unit FL and the movement of the fluid in the fluid processing unit FL will be described below with reference to FIG. 15.

Figure 13:
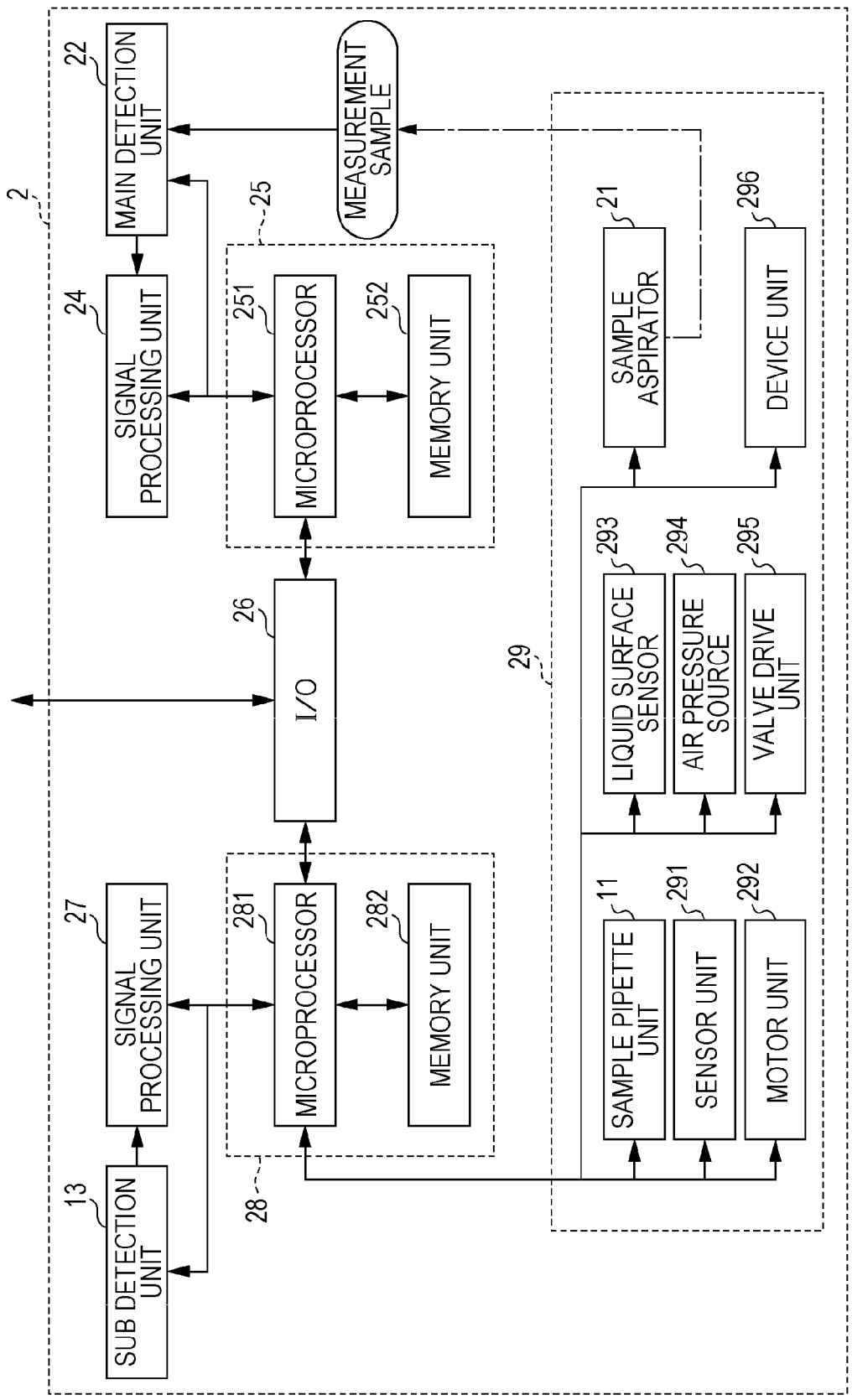
FIG. 13 is a view showing the structure of the measurement device according to the embodiment.

FIG. 13 shows the structure of the measurement device 2.

The measurement device 2 includes a main detection unit 22, sub detection unit 13, as shown in FIG. 2, and a preparation device 29 which incorporates each part for automatically preparing a sample as described above. The measurement device 2 also includes a signal processing unit 24, measurement control unit 25, I/O interface 26, signal processing unit 27, and preparation control unit 28.

The main detection unit 22 outputs forward scattered light signals (FSC), side scattered light signals (SSC), and fluorescent light signals (SFL) from the measurement sample. The signal processing unit 24 processes the signals FSC, SSC, and SFL output from the main detection unit 22, and output the result to the measurement control unit 25. The measurement control unit 25 includes a microprocessor 251 and a memory unit 252. The microprocessor 251 is connected to the data processing device 3 and the preparation control unit 28 through the I/O interface 26. The signals FSC, SSC, and SFL are transmitted to the data processing device 3 by the microprocessor 251.

Note that the data processing device 3 obtains the characteristic parameters of the forward scattered light intensity and the side fluorescent light intensity based on the signals FSC, SSC, SFL, and generates frequency distribution data for analyzing the cell and nucleus based on the characteristic parameters. The data processing device 3 performs the discrimination process on particles in the measurement sample based on the frequency distribution data, and determines whether the cells to be analyzed are abnormal, that is, specifically cancerous cells (atypical cells).

The sub detection unit 13 is configured to obtain the forward scattered light signal (FSC), and outputs signals for counting the number of cells of sufficient size to correspond to surface layer cells and intermediate layer cells based on the signal FSC. The signal processing unit 27 processes the signal FSC output from the sub detection unit 13 and outputs the signal to the preparation control unit 28. The preparation control unit 28 includes a microprocessor 281 and a memory unit 282. The microprocessor 281 is connected to the preparation device 29, and is connected to the data processing device 3 and the measurement control unit 25 through the I/O interface 26.

The preparation device 29 includes a sensor unit 291, motor unit 292, liquid surface sensor 293, air pressure source 294, and valve drive unit 295, sample pipette unit 11, and sample aspirator 21 shown in FIG. 2. A device unit 296 includes the other devices shown in FIG. 2. Each part of the preparation device 29 is controlled by the preparation control unit 28, and the signals output from each part of the preparation device 29 are output to the preparation control unit 28.

The sensor unit 291 includes sensors 121, 122, 171, and 172 shown in FIG. 3. The motor unit 292 includes a motor 141 shown in FIG. 4A and a step motor connected to the pulley 182 shown in FIG. 4B. The liquid surface sensor 293 is connected to pins 212 to 214 shown in FIG. 5C. The air pressure source 294 includes a negative pressure source P11, positive pressure source P12, and positive pressure source for the flow of the liquid (diluent, washing liquid) within the fluid processing unit FL. The valve drive unit 295 includes a mechanism for electromagnetically driving the regulator P13 and each valve in the fluid processing unit FL shown in FIG. 12.

Figure 14:
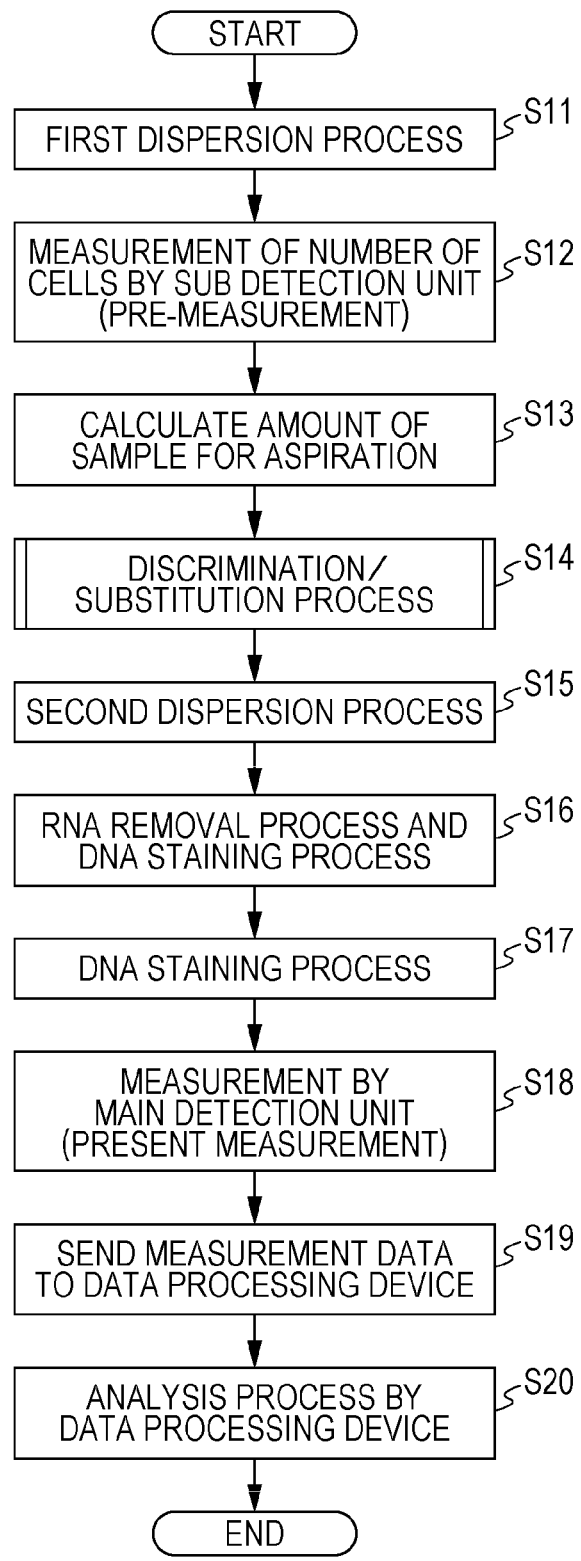
FIG. 14 is a flow chart showing the analysis operation of the canceration information providing apparatus according to an embodiment.

FIG. 14 is a flow chart showing the analysis operation performed by the canceration information providing apparatus 1.

When the canceration information providing apparatus 1 performs analysis, the user places the sample container 4 which holds a mixture of cells collected from a subject and a stock solution with a main component of methanol in the sample receiver 2a (refer to FIG. 2), and the canceration information providing apparatus 1 then starts the analysis.

When the measurement starts, the preparation control unit 28 of the measurement device 2 performs a first dispersion process on aggregated cells in the sample via the first dispersion unit 12 (S11). When the first dispersion process ends, the preparation control unit 28 detects the number of cells to be analyzed via the sub detection unit 13 (pre-measurement) (S12), and calculates the concentration of cells to be analyzed in the sample from the number of cells to be analyzed obtained in the pre-measurement and the volume of the sample supplied to the sub detection unit 13. The preparation control unit 28 then determines the required amount of sample to aspirate for the main measurement based on the calculated concentration (S13). The preparation control unit 28 then controls the discrimination/replacement unit 14 to perform the discrimination/replacement process (S14). The discrimination/replacement process will be described below with reference to FIG. 15.

The preparation control unit 28 then performs a second dispersion process on the aggregated cells in the sample via the second dispersion unit 16 (S15). The preparation control unit 28 then adds reagent (RNase) to the sample from the first reagent adding unit 19, heats the measurement sample container 5 which contains the sample via the reactor 18, and performs the RNA removal process on the cells to be analyzed in the measurement sample container 5 (S16). The preparation control unit 28 then adds reagent (stain) to the sample from the second reagent adding unit 20, heats the measurement sample container 5 which contains the sample via the reactor 18, and performs the DNA staining process on the cells to be analyzed in the measurement sample container 5 (S17).

The preparation control unit 28 controls the sample aspirator 21 to aspirate the measurement sample that has been processed for DNA staining, moves the aspirated measurement sample to the main detection unit 22, and the measurement control unit 25 controls the main detection unit 22 to perform the main measurement of the cells in the measurement sample (S18). The measurement control unit 25 transmits the measurement data obtained in the main measurement to the data processing device 3 (S19). When the data processing device 3 receives the measurement data from the measurement device 2, the analysis process is performed based on the received measurement data (S20), and the analysis results are displayed on the display unit 32.

Figure 15:
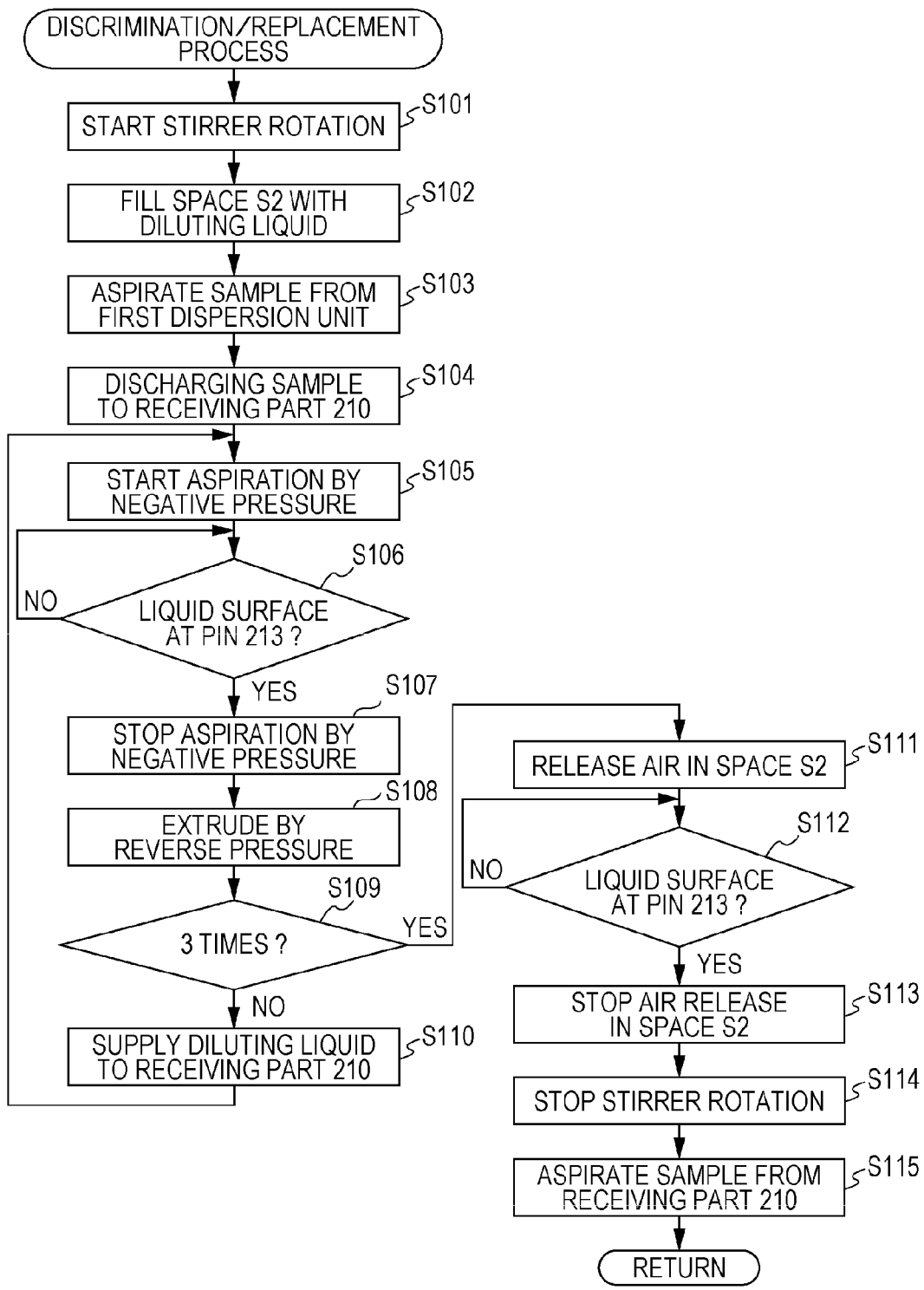
FIG. 15 is a flow chart showing the discrimination/substitution process according to an embodiment.

FIG. 15 is a flow chart showing the discrimination/substitution process, FIGS. 16A to 16I schematically shows the condition of the liquid in the receiving part 210 and the spaces S1 and S2.

When the discrimination/substitution process starts, the piston 160 and the filter member F are in the condition indicated in FIG. 11C, and the interior of the receiving part 210 and the spaces S1 and S2 are washed. Referring to the washing operation in FIG. 12, diluent is supplied into the spaces Ss and S2 through the holes H23 and H33, respectively, and washing liquid and diluent are respectively supplied into the receiving part 210 through the holes H11 and H12. The waste liquid in the space S1 is moved to the receiving part 210 through the holes H22 and H14, and the waste liquid in the receiving part 210 is discarded through the holes H13, H15, and H16, whereas the waste liquid in the space S2 is discarded through the holes H31 and H34. Hence, the condition of the liquid is as shown in FIG. 16A.

The preparation control unit 28 then closes the valves V11 to V15, V21 to V26, then closes the flow path on the air release side of the valve V16, and closes the flow path on the positive pressure source P12 side of the valve V17, and starts rotation of the stirrer R (S101). Then, the preparation control unit 28 fills the space S1 with diluent (S102).

Specifically, the valve V24 is first opened, then the diluent is supplied through the hole H23 into the space S1, in step S101. The diluent flows through the flow path 241 into the receiving part 210 at this time. When a predetermined time has elapsed after the liquid surface reaches the height of the pin 212, the valve V24 is closed and the diluent supply operation stops. Thus, the liquid surface attains the condition shown in FIG. 16B. The valves V13 and V15 are then opened, and the diluent in the space S1 and the receiving part 210 is aspirated through the filter F4 to the space S2 by applying a negative pressure in the space S2 through the hole H31 via the negative pressure source P11. When the space S2 is filled with diluent, the valves V13 and V15 are closed. Therefore, the diluent fills the space S2 as shown in FIG. 16C.

The preparation control unit 28 then aspirates the sample from the sample receiving part 12a of the first dispersion unit 12 via the sample pipette unit 11, the amount of sample aspirated having been determined in step S13 of FIG. 14 (S103). Then, the preparation control unit 28 inserts the pipette 11a from above the top plate 120 into the receiving part 210 through the hole 120b and the insertion opening 211, and discharges the sample aspirated in S103 into the receiving part 210 (S104). Thus, the liquid surface attains the condition shown in FIG. 16D.

The preparation control unit 28 then applies a negative pressure in the space S2, and starts aspirating the liquid (diluent and sample) in the receiving part 210 and the space S1 (S105). Specifically, the valves V13 and V15 are opened, and the liquid in the space S1 and the receiving part 210 is aspirated through the filter F4 to the space S2 by applying a negative pressure in the space S2 via the negative pressure source P11. When a predetermined time has elapsed after the liquid surface in the receiving part 210 reaches the height of the pin 213 (S106: YES) as shown in FIG. 16E, the preparation control unit 28 then closes the valves V13 and V15 and stops the aspiration via the negative pressure (S107). Thus, the liquid surface attains the condition shown in FIG. 16F.

Then, the preparation control unit 28 applies a reverse pressure (positive pressure) within the space S2, and extrudes the cells aggregated in the holes of the filter F4 and the cells adhered to the surface of the filter F4 on the space S1 side into the space S1 (S108). Specifically, the flow path is opened on the positive pressure source P12 side of the valve V17, and the cells are extruded into the space S1 by applying a positive pressure in the space S2 via the positive pressure source P12. When the extrusion via the reverse pressure ends, the flow path is closed on the positive pressure source P12 side of the valve V17.

When the processes of S105 to S108 are performed a first time or a second time (S109: NO), the preparation control unit 28 then supplies the diluent to the receiving part 210 (S110). Specifically, the valve V24 is opened, and then the diluent is supplied through the hole H23 into the space S1. The diluent flows through the flow path 241 into the receiving part 210 at this time. When a predetermined time has elapsed after the liquid surface reaches the height of the pin 212, the valve V24 is closed and the diluent supply operation stops. Thus, the liquid surface attains the condition shown in FIG. 16D. The process then returns to S105 and the processes of S105 to S108 are repeated three times.

The stock solution mainly composed of methanol contained in the sample is thus replaced with diluent, and foreign substances and cells other than cells to be analyzed included in the sample are discriminated. A concentrated liquid of cells to be analyzed is thus generated in the space S1.

When the processes of S105 to S108 are repeated three times (S109: YES), the preparation control unit 28 then releases the air in the space S2 (S111). Specifically, from the condition of the liquid level shown in FIG. 16F, the liquid in the space S1 is moved to the receiving part 210 side by opening the valve V16 and the flow path on the air release side of the valve V17, and applying an atmospheric pressure in the space S2. When the liquid surface in the receiving part 210 reaches the height of the pin 213 (S112: YES), the preparation control unit 28 then closes the valve V16 and the flow path on the air release side of the valve V17, stops the air release in the space S2 (S113), and stops the rotation of the stirrer R (S114).

Thus, the concentrated liquid of cells to be analyzed produced in the space S1 is moved from the space S1 to the receiving part 210, and the liquid surface attains the condition shown in FIG. 16G. The concentrated liquid of cells to be analyzed is retained below the receiving part 210. The concentration of the concentrated liquid at this time is the highest under the receiving part 210, and decreases as the liquid flows from below the receiving part 210 toward the space S1.

Then, the preparation control unit 28 inserts the pipette 11a into the deepest part of the receiving part 210 through the hole 120b and the insertion opening 211 from above the top plate 120 as shown in FIG. 16H. The preparation control unit 28 aspirates the concentrated liquid retained in the deepest part of the receiving part 210 through the pipette 11a (S115). Thus, the liquid surface attains the condition shown in FIG. 16I. The discrimination/substitution process then ends, and the processes subsequent to S15 of FIG. 14 are performed based on the concentrated liquid aspirated by the pipette 11a in S115.

Note that in the condition shown in FIG. 16H, some concentrated liquid remains in the space S1 and the flow path 241 as shown in FIG. 16I when the aspiration by the pipette 11a ends because the air is not released in the space S2.

According to the present embodiment, the liquid in the space S1 is configured to be moved to the space S2 through the filter F4 by using the negative pressure. Thus, the liquid present in the space S1 can be completely aspirated on the space S2 side, and the amount of cells other than the cells to be analyzed remaining in the space S1 can be reduced as much as possible. In the discrimination/replacement unit 14, the cells to be analyzed can be subjected to a concentration process using negative and positive pressures without moving the filter F4. Thus, the concentration process can be performed rapidly. Thus, the production efficiency of the concentrated liquid of cells to be analyzed can be improved. The concentrated liquid can be recovered in a large amount. The more amount of concentrated liquid can be subjected to analysis. The analysis accuracy of cells can be thus increased.

According to the present embodiment, the space S1 formed by the concavity 230 and the space S2 formed by the concavity 162 are liquid-tightly connected to each other through the filter F4 before the aspiration via the negative pressure starts (S105 of FIG. 15). Thus, the liquid and the sample in the space S1 can be moved to the space S2 without any leakage by using the negative pressure.

According to the present embodiment, the aspiration via the negative pressure is performed in the condition where the spaces S1 and S2 are filled with diluent through the hole H23. Thus, the use of a low negative pressure allows the liquid and the sample in the space S1 to move to the filter F4 side, and thus prevents the cells to be analyzed from passing through the filter F4.

According to the present embodiment, an atmospheric pressure is applied in the space S2 by opening the valves V16 and V17 in the flow path linked to the hole H32 formed in the concavity 162. The liquid containing the cells to be analyzed in the space S1 is thus moved to the receiving part 210 through the hole H22.

According to the present embodiment, the stirrer R formed in the concavity 230 is rotated along the side surface (filtration surface) on the concavity 230 side of the filter F4 so that a sample flow rotating along the surface of the filter F4 on the space S1 side can be generated. Therefore, the cells to be analyzed adhered to the filter F4 can be smoothly detached from the filter F4.

According to the present embodiment, the concavity 230 has the circular inner surface 232, the stirrer R rotates on the center axis A of the inner surface 232, and the reservoir 233 is formed as a concavity in a direction from the center axis A on the inner surface 232. During the discrimination/ substitution process, the cells to be analyzed included in the sample in the space S1 are thus accumulated in the reservoir 233 by the rotation of the stirrer R. Therefore, the concentrated liquid of the cells to be analyzed can be efficiently removed from the hole H22 formed in the reservoir 233.

Figure 11:
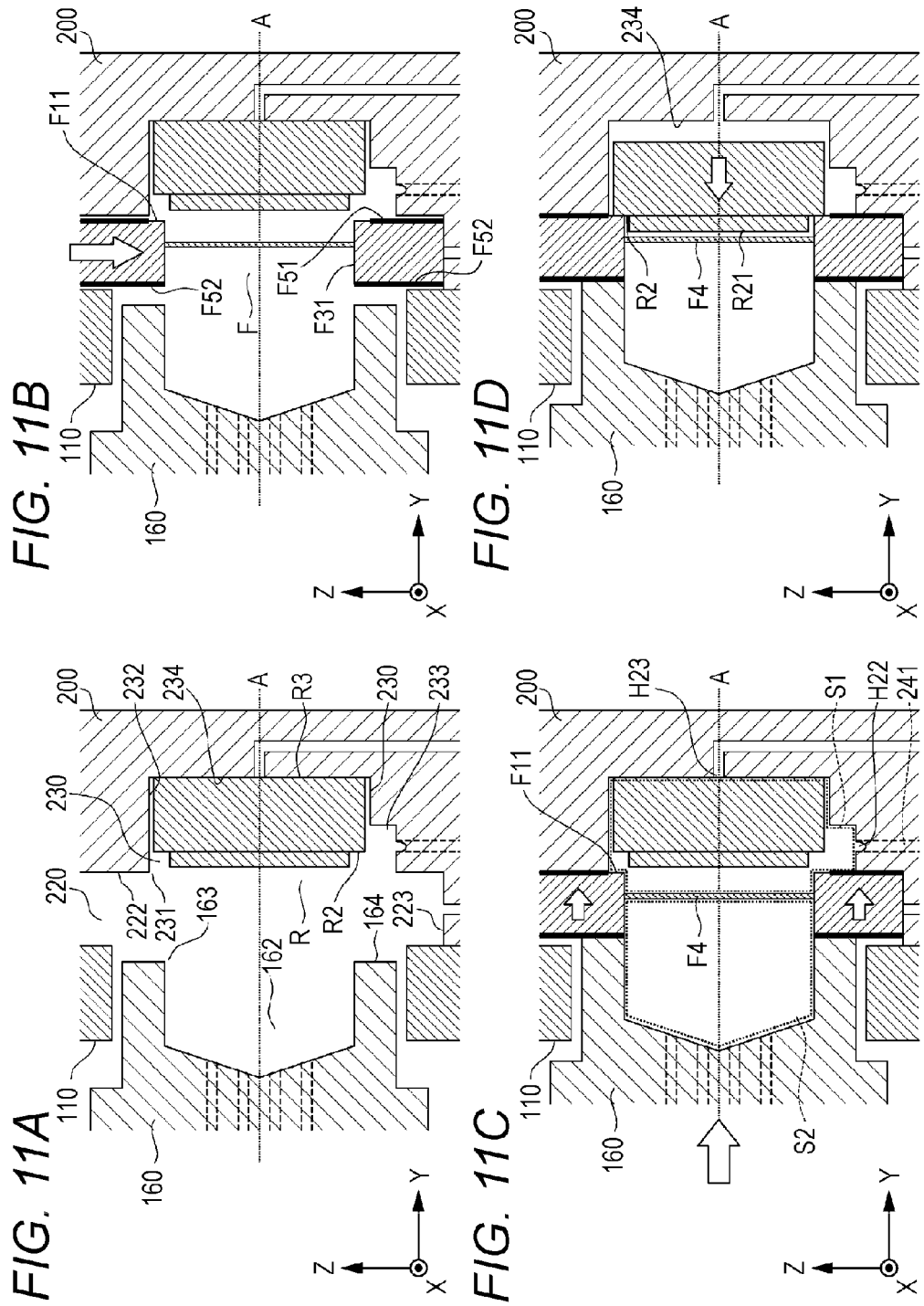
FIGS. 11A to 11D show the sequence of installing the filter member according to the embodiment.

According to the present embodiment, as shown in FIG. 10, the filter F4 is installed on the cylindrical inner surface F31 of the filter member F so that the distance between the filter F4 and the surface F1 is d22. The diameter d12 of the inner surface F31 is larger than the diameter d11 of the convexity R21 including the flange R21a of the stirrer R, and is smaller than the diameter d13 of the circumference of the surface R2 of the stirrer R. Thus, even when the stirrer R is moved to the filter member F side as shown in FIG. 11 (d), abutting of the convexity R21 against the filter F4 is prevented by the surface R2. Accordingly, damage to the filter F4 can be avoided. Since abutting of the convexity R21 against the filter F4 is prevented, the width in the Y axis direction between the concavity 230 and the stirrer R can be set so as to move the convexity R21 closer to the filter F4. Therefore, the cells to be analyzed adhered to the filter F4 can be efficiently detached from the filter F4.

According to the present embodiment, the filter F4 is provided in the filter member F, and the filter member F is inserted between the concavity 230 and the concavity 162 through the hole 120b shown in FIG. 3 and the insertion opening 221 of the receiving part 220 shown in FIG. 5A. The filter F4 is disposed at a position opposing (Y axis negative direction side) the opening 231 of the concavity 230 at this time. Thus, the filter member F is a consumable part and is easily replaced through the hole 120b and the insertion opening 221.

According to the present embodiment, the filter member F inserted between the concavity 230 and the concavity 162 through the insertion opening 221 is press-fit against the concavity 230 by moving the piston 160 for forming the concavity 162 in the Y axis positive direction. Thus, the concavity 230 and the concavity 162 are connected through the filter member F. As shown in FIG. 11C, the closed space S1 can be easily formed in the concavity 230.

According to the present embodiment, the filter member F is arranged with the filtration surface of the filter F4 parallel to the XZ plane. Therefore, when the filtration surface of the filter F4 is arranged parallel to the vertical direction, the discrimination/replacement unit 14 can be made more compact in the horizontal direction compared to when the filtration surface of the filter F4 is arranged parallel to the horizontal direction. Therefore, the measurement device 2 can be more compact in the horizontal direction, and the installation area of the canceration information providing apparatus 1 including the measurement device 2 can be made smaller. The cells to be analyzed adhered to the filter F4 are easily detached from the filter F4 by gravity.

According to the present embodiment, the hole H22 is formed below the concavity 230. Thus, the cells to be analyzed detached from the filter F4 are easily accumulated near the hole H22 by gravity. Accordingly, the cells to be analyzed can be efficiently recovered through the hole H22.

According to the present embodiment, a mixture of cells collected from a subject and a stock solution with a main component of methanol is discharged into the receiving part 210. The sample discharged into the receiving part 210 passes through the flow path 241, and then flows into the concavity 230 through the hole H22. When the valve V24 is opened, the diluent flows into the concavity 230 through the hole H23. Thus, the stock solution in the space S1 can be replaced with the replacement liquid. The space S1 can be closed to the outside by closing the valve V24.

According to the present embodiment, as shown in FIG. 7A, when to the holding member F100 is integrated with the holding member F200 by fitting the holding member F200 into the holding member F100 while allowing the filter F4 to intervene between the holding members F100 and F200, the filter F4 is sandwiched between the holding members F100 and F200 and thus the filter F4 is attached to the filter member F. Since the elastic bodies F140 and F240 are closely attached to the filter F4 at this time, the filter F4 is liquid-tightly and fixedly sandwiched between the holding members F100 and F200. According to the filter member F of the present embodiment, the filter F4 can be installed in the filter member F by the inexpensive and simple operation, while allowing the filter F4 more fixedly attached to the filter member F. Therefore, it is possible to keep down the manufacturing cost of the filter member F.

According to the present embodiment, the retainer F231 of the protruding part F230 is engaged with the engaging part F131 as shown in FIG. 8E. Since the holding member F200 is thus fixed to the holding member F100, the filter F4 can be more fixedly attached to the filter member F.

According to the present embodiment, the thick part F42 is formed on the surface of the filter F4 which is in contact with the elastic bodies F140 and F240 as shown in FIG. 7A. Thus, the thickness of the filter F4 is larger at the portion sandwiched between the holding members F100 and F200 so that breakage of the filter F4 can be suppressed.

According to the present embodiment, the filter member F is asymmetrically shaped in the X axis direction (width direction) by forming the slot F6, as shown in FIGS. 6A and 6B and FIGS. 8C and 8D. Thus, when the receiving part 220 is attached to the filter member F, the asymmetry of the filter member F is detected by the sensors 121 and 122. It is thus possible to determine whether the filter member F is appropriately attached in a state that both sides of the filter are properly placed.

According to the present embodiment, the holes F120 and F220 are configured to have a circular shape as shown in FIGS. 7A to 8E. Thus, when the holding member F100 is integrated with the holding member F200, a cylindrical part having cylindrical inner surfaces F121 and F221 are configured by the holes F120 and F220. Thus, the cells adhered to the filter F4 can be detached from the filter F4 easily and efficiently by rotating the stirrer R.

According to the present embodiment, the rubber F51 is stuck to the surface F152 of the holding member F100 as shown in FIGS. 8A and 8C. Thus, the liquid tightness between the filter F4 and the wall 222 of the receiving part 220 is improved.

According to the present embodiment, the rubber F51 is stuck away from the boundary of the hole F120 (inner circumference of the surface F151) as shown in FIG. 8C. Thus, the stirrer R can be smoothly driven without being prevented by the rubber F51, while improving the liquid tightness between the filter F4 and the wall 222 of the receiving part 220.

According to the present embodiment, the rubber F52 is stuck to the surface F210 of the holding member F200 as shown in FIGS. 8B and 8D. Thus, the liquid tightness between the filter F4 and the surface 164 of the piston 160 is improved.

According to the present embodiment, the top edge F102 is formed on the top part of the holding member F100. When the receiving part 220 is attached to the filter member F, the top edge F102 is configured to protrude into the top part of the hole 120b of the top plate 120 together with the top part of the filter member F. Thus, when the top edge F102 is gripped to take out the filter F4 from the receiving part 220, the user's fingers hit the top edge F102, and the holding member F100 is easily caught on the fingers. Thus, the filter member F can be taken out easily.

Although the present invention has been described by way of the above embodiment, the present invention is not limited to this embodiment and may be variously modified.

For example, although cervical epithelial cells are designated as the cells to be analyzed in the above embodiment, other epithelial cells such as oral cavity, bladder or pharynx; and epithelial cells of organs may be used as cells to be analyzed to determine the canceration of the cells.

Although abutting of the convexity R21 against the filter F4 is prevented by the surface R2 of the stirrer R as shown in FIG. 11D in the above embodiment, the present invention is not limited to this embodiment inasmuch as the diameter of the body R1 may be configured to be equal to the diameter d11 of the convexity R21, and a plurality of projections radially protruding into the center axis A may be formed between the convexity R21 and the body R1. In this instance, the projections prevent the convexity R21 from abutting the filter F4.

In the above embodiment, the reservoir 233 is formed below the inner surface 232 of the concavity 230. Instead of this configuration, the hole H22 may be formed below the inner surface 232 without forming the reservoir 233 on the inner surface 232. In this instance, the stirrer R is rotated so that the cells to be analyzed included in the sample in the space S1 can be accumulated near the hole H22 according to gravity. However, as shown in the above embodiment, the cells to be analyzed can be accumulated more effectively when the reservoir 233 is formed.

Although the measurement device 2 performs measurements of cells to be analyzed and the data processing device 3 performs analyses based on the measurement data in the above embodiment, the present invention is not limited to this arrangement inasmuch as these two devices may be combined in an integrated apparatus so as to combine the measurement and analysis of cells to be analyzed.

In the above embodiment, preparation of a measurement sample is performed by the preparation control unit 28, sub detection unit 13, signal processing unit 27, and preparation device 29 as shown in FIG. 13, and measurement of the measurement sample is performed by the measurement control unit 25, main detection unit 22, and signal processing unit 24. However, the present invention is not limited to this arrangement inasmuch as the device for performing the preparation of the measurement sample and the device for performing measurements may be separate devices.

In the above embodiment, the protruding parts F230 are formed on the holding member F200, and the engaging parts F131 which engage with the retainers F231 of the protruding parts F230 are formed on the holding member F100. However, the present invention is not limited to this arrangement inasmuch as the protruding parts may be formed on the holding member F100, and the engaging parts which engage with the retainers of the protruding parts provided on the holding member F100 may be formed on the holding member F200.

Although the filter member F is asymmetrically shaped in the X axis direction (width direction) by forming the slot F6 in the above embodiment, the present invention is not limited to this arrangement inasmuch as the filter member F may be asymmetrically shaped in the Y axis direction (thickness direction).

For example, as shown in FIGS. 17A and 17B, a flange F7 may be formed on the surface F101 on the Y axis positive side of the filter member F without forming the slot F6 in the filter member F shown in FIGS. 8C and 8D. In this instance, limit sensors are installed near the top plate 120 in place of the sensors 121 and 122. Thus, it is possible to determine whether the filter member F is appropriately attached in a state that both sides of the filter member are properly placed by the limit sensors.

In the above embodiment, the top edge F102 having a thickness larger than that of the portion on the longitudinally inner side is formed on the top part of the filter member F by forming the surface F101 which is one step lower than the peripheral surface on the filter member F. However, the configuration for easily taking out the filter member F is not limited to this embodiment. For example, as shown in FIGS. 17C and 17D, a protruding line portion F103 which protrudes in the Y axis positive and negative directions may be formed on the top edge of the holding member F100. As shown in FIGS. 17E and 17F, a deformed part F104 having a recess near the center in the Z axis direction may be formed on the top part of the holding member F100. Like the top edge F102, protruding line portion F103, and deformed part F104, the position which is easily caught on the fingers may be another position so long as the position is a position exposed to the outside when the receiving part 220 is attached to the filter member F.

In the above embodiment, a barcode or RFID for identifying the individual filter member F may be adhered to the top part of the filter member F. Thus, the precision of the filter member F can be easily managed and suitable replacement of the filter member F can be performed in this way.

Figure 18A:
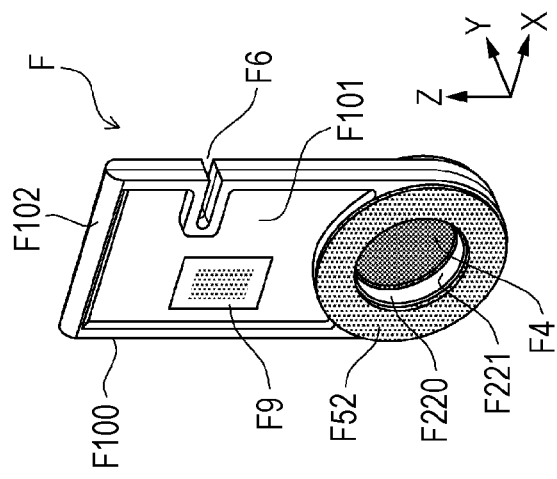
FIGS. 18A and 18B are views showing the structure of the filter member according to a modified example.

FIG. 18A shows the filter member F to which a barcode label F8 is adhered. A barcode with information (for example, the period of use) relating to the filter member F is printed on the barcode label F8. When the filter member F is used, the filter member F is installed in the receiving part 220 after reading the barcode of the barcode label F8 using a barcode reader connected to the data processing device 3. Therefore, the individual filter member F can be identified, and the period of use of the filter member F can be managed in the data processing device 3.

Figure 18B:
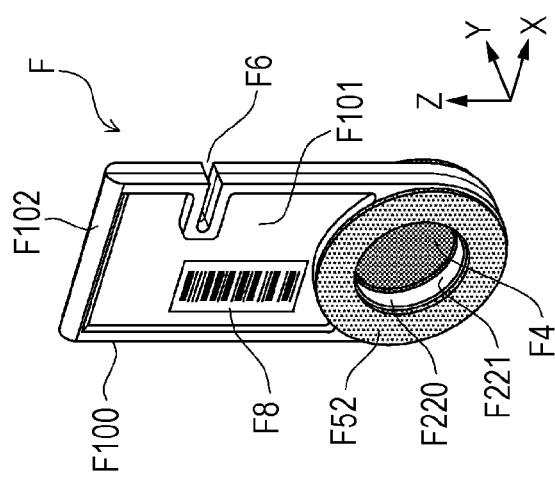

FIG. 18B shows the filter member F to which an RFID tag F9 is adhered. The information (for example, the period of use) relating to the filter member F is recorded in the RFID tag F9. In the configuration example, when the receiving part 220 is installed in the filter member F, the RFID tag F9 is automatically read by an antenna mounted near the receiving part 220. Therefore, in the data processing device 3, the individual filter member F can be identified, and the period of use of the filter member F can be managed.

Although it is possible to detect whether the filter member F is properly installed based on the output from the sensors 121 and 122 in the above embodiment, the detection results may be displayed on the display unit 32 of the data processing device 3. For example, when the filter member F is not placed properly, the state of the improper installation may be displayed on the display unit 32.

FIG. 19A is a flow chart showing an example of a process in the measurement device 2 when determining the installation condition of the filter member F, FIG. 19B is a flow chart showing an example of a process in the data processing device 3 when determining the installation condition of the filter member F, and FIG. 19C shows an example of a display when the filter member F is not placed properly. The process of FIG. 19A is performed by the preparation control unit 28 of the measurement device 2.

Referring to FIG. 19A, the preparation control unit 28 first determines whether the light receiver of the sensor 121 stops receiving light based on the signals from the sensor unit 291 (S201). When the light receiver of the sensor 121 stops receiving light (S201: YES), the preparation control unit 28 starts a timer (S202) and determines whether a predetermined time has elapsed from the time of stopping of receiving light by the light receiver of the sensor 121 (S203). When a predetermined time has elapse after the timer starts (S203: YES), the preparation control unit 28 determines whether the light receiver of the sensor 122 receives light at the timing (S204).

When the light receiver of the sensor 122 receives light (S204: YES), the preparation control unit 28 determines that the filter member F is installed properly, and terminates the process. On the other hand, when the light receiver of the sensor 122 does not receive light (S204: NO), the preparation control unit 28 determines that the filter member F is not installed properly and transmits the error data indicating the state of the improper installation to the data processing device 3.

Referring to FIG. 19B, when the error data is received (S301: YES), the data processing device 3 displays the error screen shown in FIG. 19C on the display unit 32 (S302). The user can find the improper installation of the filter member F by looking at the screen. The user installs the filter member F again while changing the direction of the filter member F, if appropriate. Thereafter, the user operates the input unit 31 and presses an OK button on the screen. When the OK button is pressed (S303: YES), the data processing device 3 clears the error screen and transmits the data indicating that the OK button has been pressed to the measurement device 2 (S304).

Returning to FIG. 19A, when the measurement device 2 receives the data indicating that the OK button has been pressed (S206: YES), the preparation control unit 28 of the measurement device 2 allows the process to return to S201 and performs the processes subsequent to S201 again. When it is determined as YES in S204, the preparation control unit 28 determines that the filter member F is installed properly, and terminates the process. Note that the operations described with reference to FIGS. 11A to 11D are performed after it is determined as YES in S204 of FIG. 19A.

According to this configuration example, the user can find that the filter member F is not installed properly, and thus it is possible to prevent the filter member F from being installed incorrectly. The user can carry out the subsequent processes smoothly by looking at the screen shown in FIG. 19C.

Note that the embodiments of the present invention may be variously modified insofar as such modifications are within the scope of technical idea being indicated in the claims.

What is claimed is:

1. A filter member comprising:
    a filter for discriminating cells to be analyzed in a sample from other components;
    a first filter holding member which comprises a first through hole and has a plate-like shape; and
    a second filter holding member which comprises a second through hole and is fitted into the first filter holding member,
    wherein
        when the first and second filter holding members are integrated by fitting the second filter holding member into the first filter holding member, the filter is sandwiched between the first filter holding member and the second filter holding member, and the first through hole is opposed to the second through hole through the filter,
        a first elastic body is formed on a surface of the first filter holding member, the surface being in contact with the filter,
        a second elastic body is formed on a surface of the second filter holding member, the surface being in contact with the filter, and
        the filter member has an asymmetrical shape by having a slot in one end in the width direction.

2. The filter member according to claim 1,
    wherein a retainer is formed and then an elastically deformable protruding part is formed on one of the first and second filter holding members, and an engaging part which is engaged with the retainer of the protruding part is formed on the other, and
    the second filter holding member is fixed to the first filter holding member by engaging the protruding part with the engaging part when fitting the second filter holding member into the first filter holding member.

3. The filter member according to claim 2,
    wherein a concavity into which the second filter holding member is fitted is formed in the first filter holding member,
    the engaging part is formed on the inner wall of the concavity, and
    the protruding part abuts the inner wall of the concavity when fitting the second filter holding member into the first filter holding member and undergoes an elastic deformation, and then when the retainer of the protruding part reaches the position of the engaging part, the protruding part undergoes an elastic recovery and the retainer is engaged with the engaging part.

4. The filter member according to claim 3,
    wherein the engaging part is formed by denting the inner wall of the concavity.

5. The filter member according to claim 1,
    wherein a thick part is formed on the surface of the filter which is in contact with the first elastic body.

6. The filter member according to claim 1,
    wherein the filter member has the asymmetrical shape in a width or a thickness direction.

7. The filter member according to claim 1,
    wherein when the first and second through holes are configured to have a circular shape, and when the second filter holding member is integrated with the first filter holding member, a cylindrical part having cylindrical inner surfaces is configured by the first and second through holes.

8. The filter member according to claim 7,
wherein the filter is situated nearer one side in the thickness direction of the filter member in the cylindrical part.

9. A filter member comprising:
a filter for discriminating cells to be analyzed in a sample from other components;
a first filter holding member which comprises a first through hole and has a plate-like shape; and
a second filter holding member which comprises a second through hole and is fitted into the first filter holding member,
wherein
when the first and second filter holding members are integrated by fitting the second filter holding member into the first filter holding member, the filter is sandwiched between the first filter holding member and the second filter holding member, and the first through hole is opposed to the second through hole through the filter,
a first elastic body is formed on a surface of the first filter holding member, the surface being in contact with the filter,
a second elastic body is formed on a surface of the second filter holding member, the surface being in contact with the filter, and
a third elastic body is formed around a circumferential portion of the first through hole which is an external surface of the first filter holding member when the first filter holding member is fitted into the second filter holding member.

10. The filter member according to claim 9,
wherein the third elastic body is formed away from the boundary of the first through hole.

11. A filter member comprising:
a filter for discriminating cells to be analyzed in a sample from other components;
a first filter holding member which comprises a first through hole and has a plate-like shape; and
a second filter holding member which comprises a second through hole and is fitted into the first filter holding member,
wherein
when the first and second filter holding members are integrated by fitting the second filter holding member into the first filter holding member, the filter is sandwiched between the first filter holding member and the second filter holding member, and the first through hole is opposed to the second through hole through the filter,
a first elastic body is formed on a surface of the first filter holding member, the surface being in contact with the filter,
a second elastic body is formed on a surface of the second filter holding member, the surface being in contact with the filter, and
a fourth elastic body is formed around a circumferential portion of the second through hole which is an external surface of the second filter holding member when the first filter holding member is fitted into the second filter holding member.

12. The filter member according to claim 1,
wherein the first filter holding member further comprises a deformed part having a larger thickness as compared to that of the longitudinal direction side near the end longitudinally away from the installation position of the filter.

13. The filter member according to claim 1,
further comprising an identifier having information relating to the filter member.

14. The filter member according to claim 13,
wherein the information relating to the filter member includes information relating to the period of use of the filter member.

15. The filter member according to claim 1,
wherein the filter is made of metal.

16. A filter member comprising:
a filter for discriminating epithelial cells in a sample from components smaller than the epithelial cells;
a first filter holding member which comprises a first through hole and has a plate-like shape; and
a second filter holding member which comprises a second through hole and is fitted into the first filter holding member,
wherein
when the first and second filter holding members are integrated by fitting the second filter holding member into the first filter holding member, the filter is sandwiched between the first filter holding member and the second filter holding member and the first through hole is opposed to the second through hole through the filter,
a first elastic body is formed on a surface of the first filter holding member, the surface being in contact with the filter,
a second elastic body is formed on a surface of the second filter holding member, the surface being in contact with the filter, and
the filter member is asymmetrically shaped by having a slot in one end in the width direction.

17. The filter member according to claim 16,
wherein the filter is porous and comprises pores having a diameter of 8 µm or more and less than 20 µm.

18. The filter member according to claim 16,
wherein the epithelial cells are cervical epithelial cells.

19. A filter member comprising:
a filter for discriminating cells to be analyzed in a sample from other components;
a first filter holding member which comprises a first through hole and has a plate-like shape; and
a second filter holding member which comprises a second through hole and is integrated with the first filter holding member,
wherein
when the first and second filter holding members are integrated, the filter is sandwiched between the first filter holding member and the second filter holding member, and the first through hole is opposed to the second through hole through the filter, and
the filter member is asymmetrically shaped by having a slot in one end in a width direction.

* * * * *